(12) United States Patent
King

(10) Patent No.: US 9,398,963 B2
(45) Date of Patent: Jul. 26, 2016

(54) NEGATIVE GAUGE PRESSURE DYNAMIC CONVECTION SYSTEM FOR ARTIFICIAL LIMB AND ASSOCIATED METHODS

(71) Applicant: Charles Russell King, Cumberland, MD (US)

(72) Inventor: Charles Russell King, Cumberland, MD (US)

( * ) Notice: Subject to any disclaimer, the term of this patent is extended or adjusted under 35 U.S.C. 154(b) by 26 days.

(21) Appl. No.: 14/222,867

(22) Filed: Mar. 24, 2014

(65) Prior Publication Data

US 2015/0265432 A1  Sep. 24, 2015

(51) Int. Cl.
| | | |
|---|---|---|
| *A61F 2/80* | (2006.01) | |
| *A61F 2/68* | (2006.01) | |
| *A61F 2/78* | (2006.01) | |
| A61F 2/76 | (2006.01) | |
| A61F 2/60 | (2006.01) | |
| A61F 2/50 | (2006.01) | |
| A61F 2/70 | (2006.01) | |
| A61F 2/74 | (2006.01) | |

(52) U.S. Cl.
CPC ... *A61F 2/80* (2013.01); *A61F 2/68* (2013.01); *A61F 2/7812* (2013.01); *A61F 2/602* (2013.01); *A61F 2/70* (2013.01); *A61F 2002/501* (2013.01); *A61F 2002/5032* (2013.01); *A61F 2002/5035* (2013.01); *A61F 2002/741* (2013.01); *A61F 2002/742* (2013.01); *A61F 2002/747* (2013.01); *A61F 2002/7655* (2013.01); *A61F 2002/7665* (2013.01); *A61F 2002/7818* (2013.01); *A61F 2002/7875* (2013.01); *A61F 2002/802* (2013.01); *A61F 2002/805* (2013.01)

(58) Field of Classification Search
CPC .................. A61F 2002/501; A61F 2002/5032; A61F 2002/5035; A61F 2002/766; A61F 2002/7655; A61F 2002/7665; A61F 2002/802; A61F 2002/805; A61F 2/70; A61F 2/602; A61F 2/80; A61F 2/7843
See application file for complete search history.

(56) References Cited

U.S. PATENT DOCUMENTS

| | | |
|---|---|---|
| 2,834,025 A | 5/1958 | Leavy |
| 3,377,416 A | 4/1968 | Kandel |
| 4,917,795 A | 4/1990 | Sable et al. |
| 5,258,037 A | 11/1993 | Caspers |
| 5,411,321 A | 5/1995 | Harness |

(Continued)

OTHER PUBLICATIONS

Klute et al., The thermal conductivity of prosthetic sockets and liners Prosthet Orthot Int., 2007, 31(3): p. 292-9 Sage, London.

(Continued)

*Primary Examiner* — Jacqueline Woznicki

(57) ABSTRACT

The negative gauge pressure dynamic convection system for artificial limb system is to be attached to a residual limb of an amputee. The device provides thermal energy transfer from within an artificial limb to the ambient atmosphere through regulated cyclical differential pressure airflow into the sealed environment between both the residuum and the inside of the suspension liner of an artificial limb and as an alternate embodiment between the rigid socket and the outside of the suspension liner or a combination of both. The system may include a multi-ply surface area multiplying textile layer; a limb-conformable convection suspension liner; an artificial limb socket with an over-molded enclosure for system components; a convection manifold assembly; a convection control system, which includes a continuously operating airflow generation device, and a rising edge triggered negative gauge pressure regulation device, such as an electromechanical binary airflow proportioning device, or an alternate mechanical binary airflow proportioning device.

31 Claims, 17 Drawing Sheets

(56) References Cited

U.S. PATENT DOCUMENTS

| | | | |
|---|---|---|---|
| 5,466,261 A | 11/1995 | Richelsoph | |
| 5,480,455 A | 1/1996 | Norvell | |
| 5,549,709 A * | 8/1996 | Caspers | A61F 2/5046 623/24 |
| 5,571,208 A | 11/1996 | Caspers | |
| 5,728,169 A | 3/1998 | Norvel | |
| 5,888,230 A | 3/1999 | Helmy | |
| 6,014,823 A | 1/2000 | Lakic | |
| 6,544,292 B1 | 4/2003 | Laghi | |
| 6,554,868 B1 | 4/2003 | Caspers | |
| 6,645,253 B2 | 11/2003 | Caspers | |
| 6,726,726 B2 | 4/2004 | Caspers | |
| 6,761,742 B2 | 7/2004 | Caspers | |
| 6,974,484 B2 | 12/2005 | Caspers | |
| 8,182,547 B2 | 5/2012 | King | |
| 8,475,537 B2 | 7/2013 | King | |
| 8,535,389 B2 * | 9/2013 | McKinney | A61F 2/7812 623/34 |
| 2001/0016781 A1 | 8/2001 | Caspers | |
| 2002/0091449 A1 | 7/2002 | Caspers et al. | |
| 2003/0181990 A1 | 9/2003 | Phillips | |
| 2004/0030411 A1 | 2/2004 | Caspers | |
| 2004/0163278 A1 | 8/2004 | Caspers et al. | |
| 2004/0167638 A1 | 8/2004 | Caspers | |
| 2005/0131549 A1 | 6/2005 | Caspers | |
| 2005/0197611 A1 | 9/2005 | Taranow | |
| 2007/0055383 A1 * | 3/2007 | King | 623/34 |
| 2007/0191965 A1 * | 8/2007 | Colvin et al. | 623/34 |
| 2009/0240344 A1 * | 9/2009 | Colvin et al. | 623/36 |
| 2010/0125342 A1 | 5/2010 | King | |
| 2010/0274364 A1 * | 10/2010 | Pacanowsky et al. | 623/36 |
| 2011/0071649 A1 * | 3/2011 | McKinney | 623/34 |
| 2011/0247321 A1 * | 10/2011 | Streeter et al. | 60/327 |
| 2012/0215324 A1 | 8/2012 | King | |

OTHER PUBLICATIONS

Hachisuka et al. "Moisture permeability of the total surface bearing prosthetic socket with a silicone liner: is it superior to the patella-tendon bearing prosthetic socket?" J. Uoeh, 2001, 23, 225-32, Kitakyūshū, Japan.

Peery, et al. Residual-limb skin temperature in transtibial sockets. J Rehabil Res Dev. 2005, 42(2): p. 147-54. Veterans Affairs, USA.

Shibasaki, et al. "Neural control and mechanisms of eccrine sweating during heat stress and exercise" J Appl Physiol, 2006. 100(5): p. 1692-701. American Physiological Society, USA.

Parsons "Human thermal environments: the effects of hot, moderate, and cold environments on human health, comfort, and performance." 2nd ed. 2003, xxiv, p. 527. Taylor & Francis. London; New York.

* cited by examiner

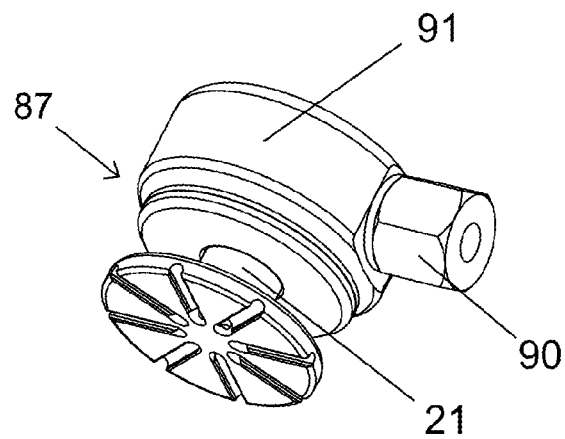
FIG. 9B
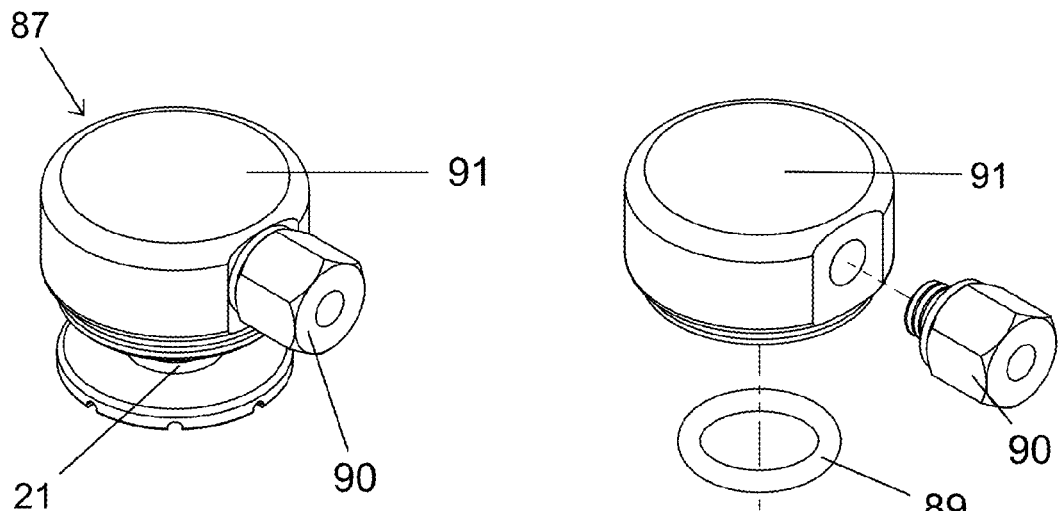
FIG. 9A
FIG. 9C

NEGATIVE GAUGE PRESSURE DYNAMIC CONVECTION SYSTEM FOR ARTIFICIAL LIMB AND ASSOCIATED METHODS

RELATED APPLICATIONS

This application claims the benefit U.S. Provisional Application Nos. 61/840,404 filed Jun. 27, 2013, 61/911486 filed Dec. 4, 2013, all of which are hereby incorporated herein in their entireties by reference.

FIELD OF THE INVENTION

The present invention relates to the field of artificial limbs, and, more particularly, liners employed in artificial limbs, related systems and related methods.

BACKGROUND OF THE INVENTION

Tests measuring the thermal conductivity of 23 different commercially available prosthetic liners and common socket materials by Klute, G. K., et al. (2007), in a paper titled "The thermal conductivity of prosthetic sockets and liners" Prosthet Orthot Int., 31(3): p. 292-9 found that all samples tested effectively trapped thermal energy. Hachisuka et al. (2001) in an article titled "Moisture permeability of the total surface bearing prosthetic socket with a silicone liner: is it superior to the patella-tendon bearing prosthetic socket?" J. Uoeh, 23, 225-32 found that an artificial limb liner seals off airflow to both the residual limb and to the prosthetic socket, which results in an accumulation of perspiration between the liner and limb.

Even relatively light activities like walking can cause substantial increases in skin temperatures inside the prosthesis as reported by Peery, J. T., et al. (2005) in the paper titled "Residual-limb skin temperature in transtibial sockets. J Rehabil Res Dev. 42(2): p. 147-54. Shibasaki, M., et al. (2006), in a paper titled "Neural control and mechanisms of eccrine sweating during heat stress and exercise" J Appl Physiol, 100(5): p. 1692-701; teaches as skin temperatures increase, the physiological response can include both vasodilation and sympathetic stimulation of the limb's sweat glands. It is of interest to note that vasodilation and sweat production continues to increase linearly with temperature as taught by Parsons, K. C., (2003) in a paper titled "Human thermal environments: the effects of hot, moderate, and cold environments on human health, comfort, and performance." 2nd ed. 2003, London; New York: Taylor & Francis. xxiv, p. 527.

It can be extrapolated from the citations above that a wearing a prosthetic limb will result in an increasing rise in skin temperature and increasing moisture accumulation. It's the insulative materials of modern prosthetic socket construction and suspension that trap heat and deprive the skin of cooling through evaporation of perspiration. There is a need for an approach to reduce thermal energy buildup in an artificial limb dynamically throughout its duration of use.

SUMMARY OF THE INVENTION

In view of the foregoing background, it is therefore an object of the present invention to provide an artificial limb system and a method to manage excessive thermal buildup and consequently reduce the amount of perspiration generated.

This and other objects, features, and advantages in accordance with the present invention may be provided by a negative gauge pressure dynamic convection artificial limb system to be attached to a residual limb of an amputee. The device provides thermal energy transfer from within an artificial limb to the ambient atmosphere through regulated cyclical differential pressure airflow into the sealed environment between both the residuum and the suspension liner of an artificial limb and as an alternate embodiment between the rigid socket and suspension liner or a combination of both. The artificial limb system may include a multi-ply surface area multiplying textile layer; a limb-conformable convection liner; an artificial limb socket, e.g. with an over molded enclosure for system components; a convection manifold assembly; a convection control system, which includes a continuously operating airflow generation device, and a rising edge triggered negative gauge pressure regulation device, such as an electromechanical binary airflow proportioning device, or an alternate mechanical binary airflow proportioning device.

The limb-conformable thermal convection liner is used for both suspension and comfort. It has longitudinal scallops or convection guides on its exterior surface that taper proximally. Its interior surface has airflow grooves to improve internal airflow efficiency. The liner may be constructed from thermally conductive silicone and its textile cover may contain phase change yarns.

An artificial limb socket is manufactured from carbon fiber or thermoplastic. It has an affixed over-molded enclosure for system components such as a battery housing, control circuits, airflow generating device, negative gauge pressure regulating device and configured for associated ports and tubing.

A convection manifold assembly may be made from a transparent material. It provides user access to a filtered mechanical pressure loss control mechanism, allows fluid communication with a pressure transducer, and contains a reservoir to collect moisture and a user accessible absorber for absorbing and removing of moisture.

The convection control system employs regulated cyclical differential pressure airflow through a continuously operating airflow generation device and a rising edge triggered negative gauge pressure regulation device. Airflow is directed inside or outside a limb conformable convection suspension liner, or a combination of both flow paths.

A continuous airflow generation device employs either a low velocity electromechanical design and associated control circuit or a mechanical design, which are specifically configured for artificial limbs and currently provided by various device manufacturers. These mechanical negative gauge pressure pumps are either actuated by body weight or the dynamics of ambulation.

A rising edge triggered negative gauge pressure regulation device employs an electromechanical or a mechanical binary proportioning device. The binary proportioning device is activated by crossing a pressure threshold resulting from rising negative gauge pressure. Upon reaching the established pressure threshold an air flow path to the atmosphere is opened. Atmospheric pressure forces air into the sealed environment, creating both a cycle of airflow and regulating the pressure in a sealed environment between the limb and liner or the liner and socket or a combination of both.

The convection control system may further comprise: a battery to power the potential embodiment of an electric negative gauge pressure generating device with circuit controller and a negative gauge pressure regulation device, embodied as an electromechanical binary airflow proportioning device with associated controller.

Objects, features, and advantages in accordance with the present invention may also be provided by a method of attaching an artificial limb to a residual limb. The method may include providing a negative gauge pressure forced convection system for an artificial limb system to be attached to a residual limb of an amputee; providing a multi-ply surface area multiplying textile layer; a limb-conformable convection liner; an artificial limb socket frame with an over-molded enclosure for system components, and a convection manifold assembly. The method may include providing a convection control system, which includes a continuously operating airflow generation device, and a rising edge triggered negative gauge pressure regulation device, such as an electromechanical binary airflow proportioning device, or alternate mechanical binary airflow proportioning designs.

The provided limb-conformable thermal convection liner is used for both suspension and comfort. It has longitudinal scallops on its exterior surface that taper proximally. Its interior surface has airflow grooves to improve internal airflow efficiency. The liner may be constructed from thermally conductive silicone and the yarns of its cover may contain phase change materials. The provided artificial limb socket may be manufactured from carbon fiber or thermoplastic, for example. It has an affixed over-molded enclosure for system components such as a battery housing, control circuits, airflow generating device, negative gauge pressure regulating device and configured for associated ports and tubing.

The provided convection manifold assembly may be made from a transparent plastic. It provides user access to a filtered mechanical pressure loss control mechanism, allows fluid communication with a pressure transducer, and contains a reservoir to collect moisture and a user accessible absorber for absorbing and removing of moisture. The provided convection control system employs regulated cyclical differential pressure airflow through a continuously operating airflow generation device and a rising edge triggered negative gauge pressure regulation device. Airflow is directed inside or outside a limb conformable convection suspension liner, or a combination of both flow paths.

The provided continuous airflow generation device employs either a low velocity electromechanical design and associated control circuit or a mechanical design, which are specifically configured for artificial limbs and currently provided by various device manufacturers. These mechanical negative gauge pressure pumps are either actuated by body weight or the dynamics of ambulation. The provided rising edge triggered negative gauge pressure regulation device employs an electromechanical or a mechanical binary proportioning device. It is activated by a pressure threshold event resulting from rising negative gauge pressure. For example, upon reaching a set pressure threshold, an air flow path to the atmosphere will be opened. Atmospheric pressure forces air into the sealed environment, creating both cyclic airflow and regulation of the pressure in a sealed environment between the limb and liner or the liner and socket or a combination of both.

The provided convection control system may further comprise: a battery to power the potential embodiment of an electric negative gauge pressure generating device with circuit controller and a negative gauge pressure regulation device, embodied as an electromechanical binary airflow proportioning device with associated controller.

The many embodiments of the present invention described herein contribute to providing thermal energy transfer (convection) from within an artificial limb to the ambient atmosphere, which directly reduces the amount of perspiration generated.

BRIEF DESCRIPTION OF THE DRAWINGS

FIG. 9A, FIG. 9B and FIG. 9C are an assembled, rotated and exploded view of a mechanical binary airflow proportioning device, which may be a feature of the forced dynamic convection system to be attached to a residual limb in accordance with the present invention.

DETAILED DESCRIPTION OF THE PREFERRED EMBODIMENTS

The present invention will now be described more fully hereinafter with reference to the accompanying drawings in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout. The dimensions of layers and regions may be exaggerated in the figures for greater clarity.

Figure 1:
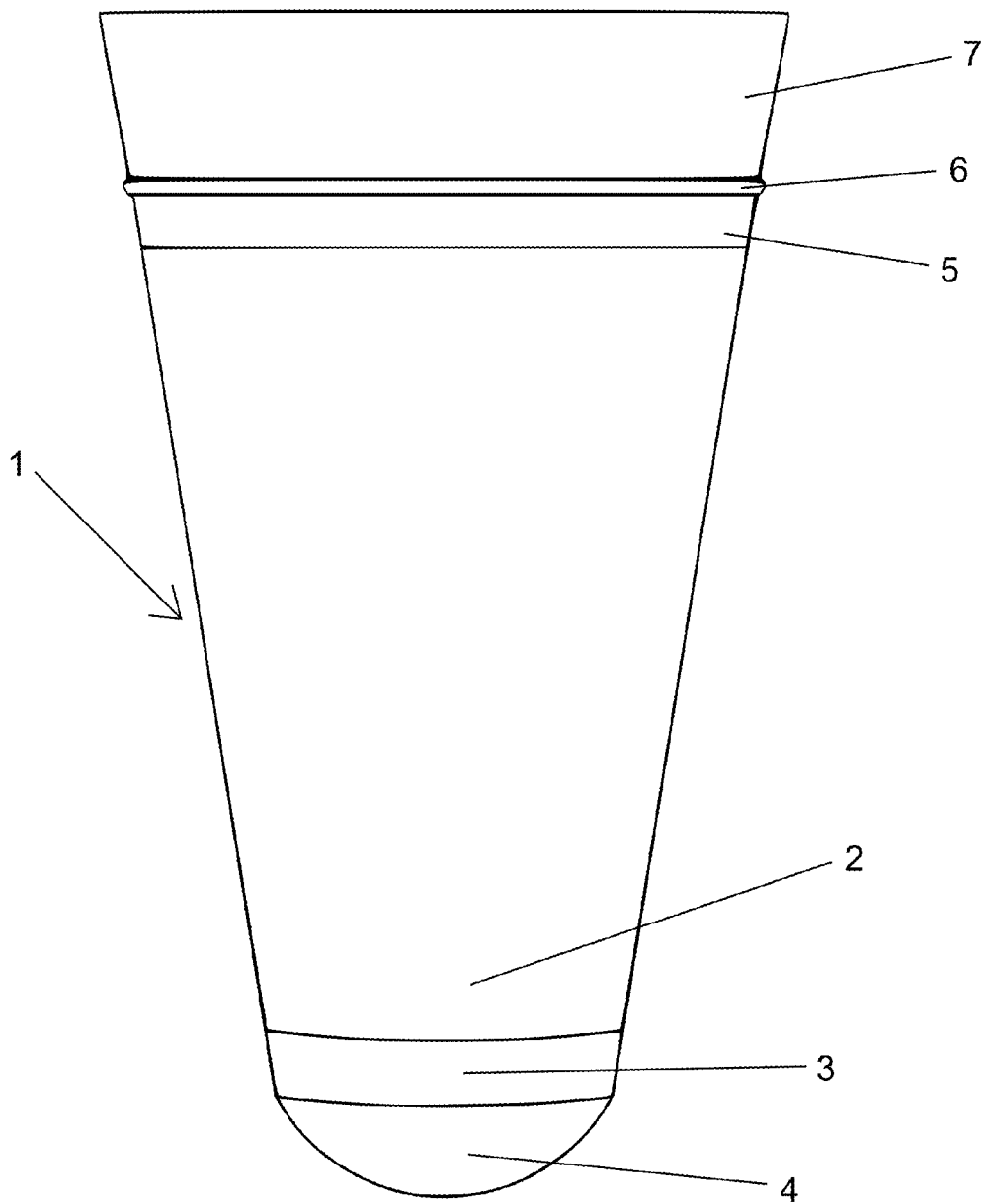
FIG. 1 is an anterior view of the surface area multiplying textile layer with proximal airflow seal to be attached to a residual limb in accordance with the present invention.

Referring initially to FIG. 1, the multi-ply surface area multiplying textile layer 1, which comprises a five ply distal end knitted layer 4, three ply knitted layer 3 and one ply knitted layer 2, a laminate transition area 5, a raised annular ring 6, and an airflow seal 7 will now be described. For example, the five ply layer 4 and the three ply layer 3 are one to two inches long and the one ply layer 2 is typically six to fourteen inches long. It is the addition of varying thickness or ply of textile material that may constitute an improvement in this existing design. The textile layer is continuously cavitated, which means the volume of the textile layer comprises interconnected cavities which are continuous with the exterior of the material, aiding airflow.

As reduced to practice in the Dynamic Air Exchange System, without the multi-ply construction, a textile layer 1, which conforms snugly to the shape of an amputee's stump is laminated with a flexible elastomeric top 7 (e.g. silicone), of such a diameter as to conform comfortably and snugly with the proximal region of an amputee's residuum. The textile layer 1 is donned directly on the amputee's stump and worn underneath the system's convection liner (described in FIGS. 2 and 4 below).

The continuously cavitated multi-ply surface area multiplying textile layer 1 surrounds at least a portion of the residual limb and defines a regulated negative gauge pressure environment between the liner and the residual limb, which facilitates airflow inside the liner as taught in U.S. Pat. Nos. 8,182,547 and 8,475,537 (to the present inventor), and hereafter will be collectively referenced as the Dynamic Air Exchange System. Negative gauge pressure (vacuum) is commonly expressed in inches of mercury ("Hg) or millimeters of mercury (mmHg), which is equal to torr. One atmosphere equals 14.7 psia (0 psig), 29.92"Hg (0"Hg absolute), 760 mmHg, 760 torr or 1,013 mbar. The airflow seal 7 of the surface area multiplying textile layer 1 includes a gently tapered laminate transition area 5, where the fibers of the textile are adherently intertwined with silicone and terminate at the raised annular ring 6. The annular ring 6 and proximal seal area 7 are preferably devoid of textile fibers, which effectively seals both pressure and airflow. As such, the airflow seal 7 is preferably an impervious seal.

An improved feature to this design is the distal multi-ply tapering construction as opposed to a single ply monolithic construction. Ply is an industry measure of textile thickness. Sanders J E et al. in the 2012 paper titled "Amputee socks: how does sock ply relate to sock thickness?" Prosthet Orthot Int. 2012 March; 36(1):77-86, found that one ply averaged 0.7 mm, three ply averaged 1.2 mm and five ply averaged 1.5 mm for similar knitted single material textile layers. Ply thickness is an industry convention, rather than a precise measure. Adding a distal toe constructed of five ply material, followed by a band of three ply material transitioning to a single ply material provides an increase in airflow cavities resulting in less air flow resistance inside the liner and thus greater airflow for the system's continuously operating airflow generation device of the convection control system. The knitted transitioning ply layers provide a smooth textile layer without seams or noticeable ply thickness distortions for user comfort and skin health.

Figures 2A, 2B:
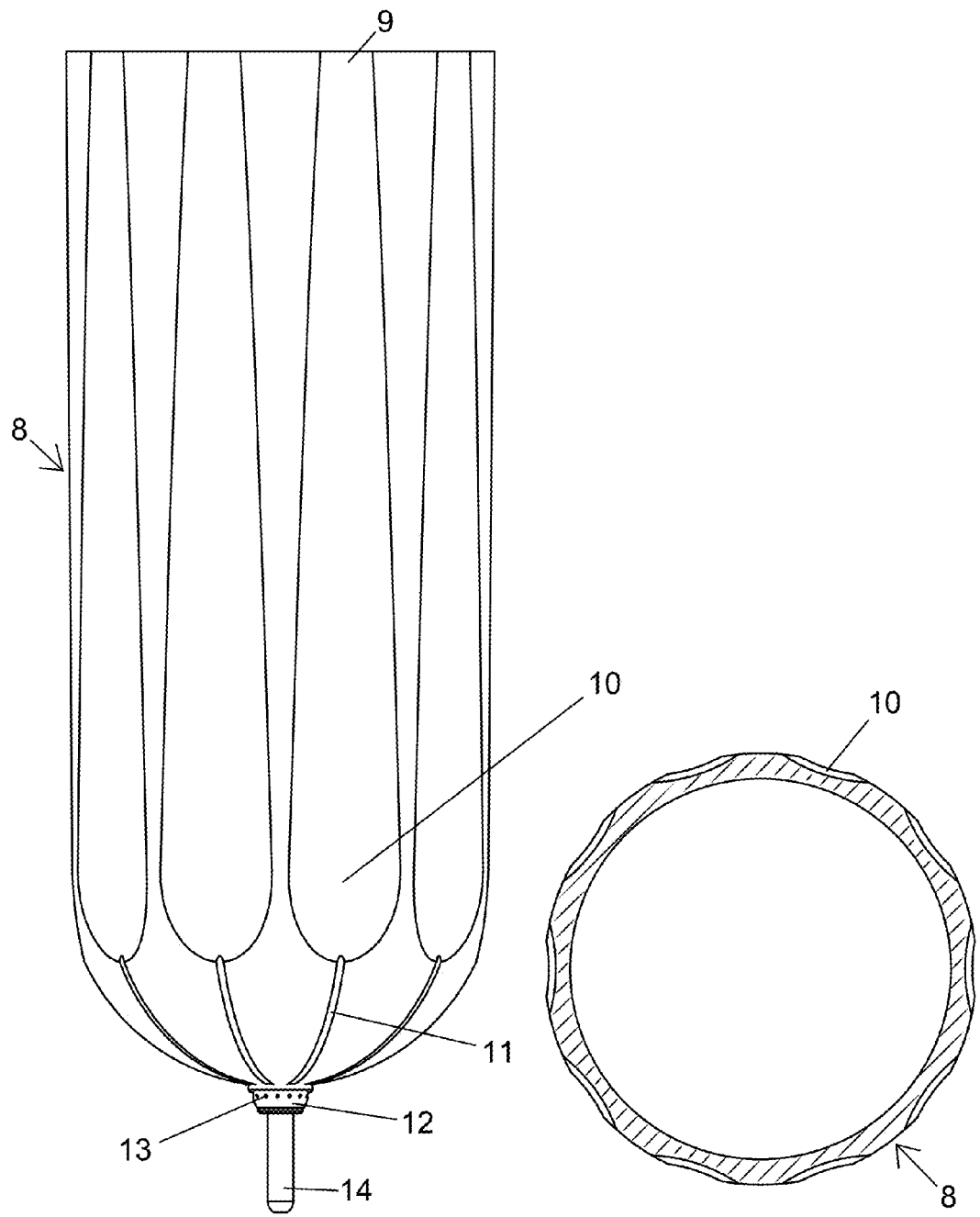
FIGS. 2A and 2B are an anterior view and a lower cross-sectional view of the convection liner to be attached to a residual limb in accordance with the present invention.

Referring initially to FIG. 2A and the lower cross-sectional view depicted in FIG. 2B, the convection liner 8, which has longitudinal scallops 10 on its exterior surface tapering proximally 9, distal exterior airflow channels 11, and configured in this depicted embodiment to have an exterior convection pin adapter 12, with convection holes 13 and a hollow convection pin 14 will now be described. The convection liner 8 for artificial limbs includes an elastomeric tubular limb-conforming flexible liner that has a plurality of longitudinal scallops 10, which taper in width and depth proximally 9 and are in fluid communication with distal exterior airflow channels 11. FIG. 2B depicts a lower cross-sectional view of the convection liner 8, which illustrates the depth of the concave scallops 10. In the embodiment depicted in FIG. 2B, the convection liner has a smooth inner surface. A removable exterior convection pin adapter 12, ported with airflow holes 13 receives a hollow convection pin 14, which attaches to a lock mechanism in the rigid socket frame of an artificial limb and comprises a distal air outflow port, which is in fluid communication with the convection manifold assembly of the negative gauge pressure forced convection system. The exterior convection pin adapter 12 has a plurality of convection holes 13 in a circular pattern, angled such that they feed into a central convection channel, feeding into the hollow convection pin 14 comprising a distal air outflow port, allowing fluid communication with the sealed or unsealed environment between the outside of the convection liner and the rigid socket frame and ultimately, the continuously operating airflow generation device of the convection control system.

In alternate embodiments, fluid communication with the continuously operating airflow generation device of the convection control system may exist with the sealed environment between the residuum and the inside of the convection liner or the sealed or unsealed environment between the rigid socket and the outside of the convection liner or a combination of both.

A convection liner without a pin, suspended by atmospheric pressure in the prosthetic socket, is a potential alternate configuration of this design. The convection liner may be donned over the surface area multiplying textile layer 1 with airflow seal 7 depicted in FIG. 1 and may include the inflow and outflow air channels and related ports in the Dynamic Air Exchange System. As depicted in FIG. 2A and FIG. 2B, the convection liner 8 is configured for only airflow over the exterior of the liner.

The minimum amount of negative pressure to hold the convection liner on the residuum as well as to suspend the liner in the artificial limb socket frame by atmospheric pressure is a function of the weight of the artificial limb divided by the cross-sectional area of the residual limb near the distal end. A typical transtibial amputee patient may require a negative gauge pressure of 38 mm Hg to securely hold their liner and artificial limb on. It should be noted that 38 mm Hg of negative gauge pressure is achievable with common suction socket designs that date back to the prior art of Dubois Parmelee, Feb. 10, 1863 U.S. Pat. No. 37,637 and were subsequently improved with auto expulsion modular valves as referenced by Charles W. Radcliffe in the 1955 article "Functional Considerations in Fitting the Above Knee Limb." Art Limbs, Vol. 2, #1 p. 35-60, which references that 77.6 mm Hg is achievable with auto expulsion modular valves. Airflow between the liner and the limb and airflow between the exterior of the liner and the artificial limb socket, created by a continuous negative gauge generation device of the convection control system requires maintaining the differential pressure level of industry standard expulsion valves (in the example above, thirty-eight mmHg) to achieve secure suspension of an artificial limb.

The longitudinal scallops 10 and distal exterior airflow channels 11 allow efficient thermal energy transfer to occur during forced dynamic convection and thus act as convection guides. The longitudinal scallops 10 also create positive volumetric distortion during stance phase. The liner expands during weight bearing, effectively increasing the volume of the socket, due to the expansion provided by the scalloped shape of the liner. This has the effect of mitigating residuum shrinkage during its duration of use. As advances in silicone and textile fabrics continue, the liner may be constructed from thermally conductive silicone and the yarns of a potential textile cover (not depicted) may contain phase change materials, further assisting convection.

Figures 3A, 3B:
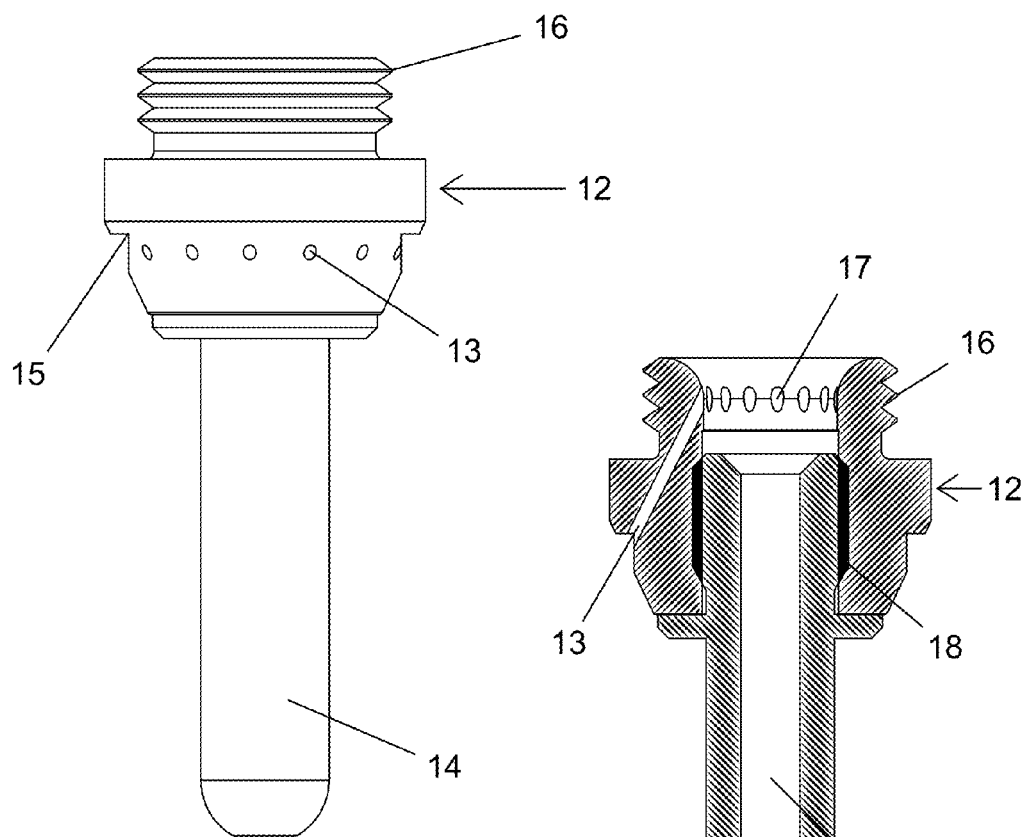
FIG. 3A and FIG. 3B are an anterior view and a cross-sectional view of the exterior convection pin adapter, a feature of the convection artificial limb liner to be attached to a residual limb in accordance with the present invention.

Referring to FIG. 3A and the cross-sectional view FIG. 3B, the exterior convection pin adapter 12 is depicted, which includes an exterior threaded section, 16 and an interior threaded section 18, airflow holes 13, wrench flats 15, a central convection channel opening 17 and an installed hollow convection pin 14. The exterior airflow convection pin adapter 12 has a plurality of airflow holes 13 in a circular pattern, angled such that they feed into a central convection channel 17, allowing fluid communication with the installed hollow convection pin 14 that comprises a distal air outflow port 19, which is in fluid communication with the convection manifold (FIGS. 6A and 6B) and ultimately the continuously operating airflow generation device. The hollow convection pin 14 has a broached distal region 20 to receive an installation tool. The proximal threaded section 16 of the exterior convection pin adapter 12, engages a receiving umbrella within the convection liner that preferably, does not have a distal air outflow port with occlusion preventing flange installed, (although such a configuration is a potential embodiment of this system). Wrench flats 15 allow secure installation as well as removal for alternately configured convection pin threaded adapters, which change the functionality of the system. In the depicted embodiment, this exterior convection pin adapter 12 allows forced convection on the outside of the convection liner by the flow of air over the exterior of the convection liner and its exterior longitudinal scallops and distal exterior airflow channels, through the convection holes 13, which collect in a central convection channel opening 17 and the travels down the distal convection channel 19 of the hollow convection pin 14, into a convection manifold and ultimately into and expelled from the continuously operating airflow generation device of the convection control system. A potential embodiment of this design would comprise the addition of a convection liner with a distal air outflow port with occlusion preventing flange installed which would allow simultaneous fluid connection between regulated the inner liner environment and the outer liner environment.

Figure 4A:
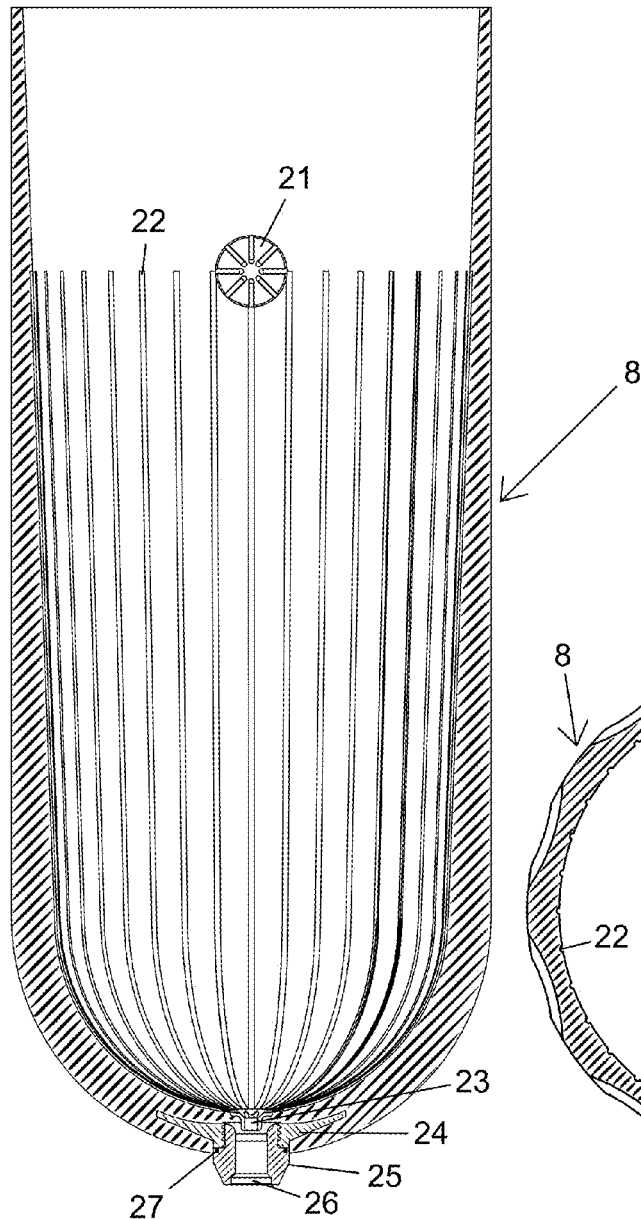
FIG. 4A and FIG. 4B are a frontal cross-sectional view and a lower cross-sectional view respectively of the airflow artificial limb liner to be attached to a residual limb in accordance with the present invention.
Figure 4B:
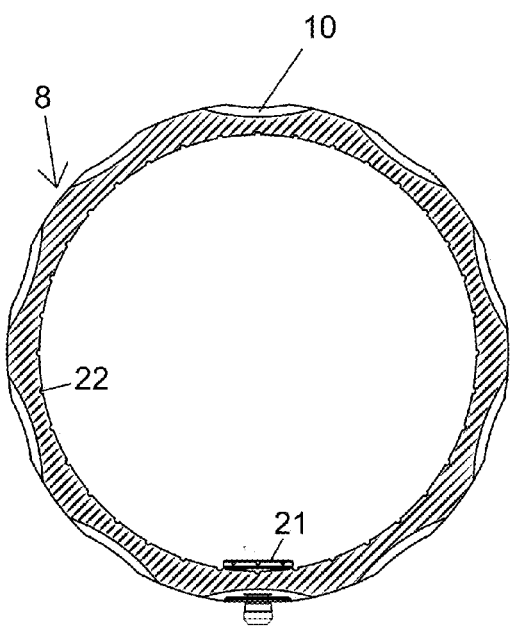

Referring to FIG. 4A and FIG. 4B, depicted is the convection liner 8 in a frontal cross-section FIG. 4A and lower cross-section FIG. 4B. In the depicted embodiment, the convection liner 8, with longitudinal scallops 10, has a plurality of internal narrow airflow grooves 22 which begin at the center level of the at least one proximal air channel inflow port with occlusion preventing flange 21, of the existing Dynamic Air Exchange System, and terminates at the distal air outflow port with occlusion preventing flange 23 also from the Dynamic Air Exchange System. The airflow grooves 22 are situated below the airflow seal and interface with the multiply surface area multiplying textile layer (depicted in FIG. 1), so that airflow is improved with these additional convection guides in the convection liner 8 and the sealed negative gauge pressure environment between both the residuum and the convection liner 8 is maintained. The airflow grooves are of a narrow width, such that invagination of the tissue does not occur when wearing the multi-ply surface area multiplying textile layer. Depicted in FIGS. 4A and 4B are longitudinal grooves, but the airflow grooves may be angled, serpentine, crosshatched, so as to direct negative gauge pressure flow evenly over the surface area of the residuum.

An alternately configured interior convection pin threaded adapter 25 threads into a receiving umbrella 24 that is adherently embedded within the liner's material construction to create a secure mounting for the convection pin adapter 25 and convection pin. The interior convection pin threaded adapter 25 has an axial O-ring gland 27 that seals along the face of the mating surfaces of the interior convection pin threaded adapter 25 and receiving umbrella 24. A sealing surface 26 receives an O-ring attached to the convection pin and creates an airtight seal. These sealing designs aim to prevent fluid communication (leaks) between the inside of the liner and the outside of the liner environment.

In this depicted embodiment, this solid interior convection pin threaded adapter 25 allows forced convection on the inside of the convection liner 8 by the flow of air through the at least one proximal air channel inflow port with occlusion preventing flange 21, over its interior surface, which is assisted by the airflow grooves 22 acting as convection guides and the multi-ply surface area multiplying textile layer, collecting at the distal air outflow port with occlusion preventing flange 23 and travels down the distal convection channel of the hollow convection pin (not depicted), into a convection manifold and ultimately into and expelled from the continuously operating airflow generation device of the convection control system. As depicted in FIGS. 4A and 4B, the convection liner 8, with the interior convection pin adapter 25 is configured for only airflow over the inside of the convection liner 8 and the residuum of an amputee.

Figure 5B:
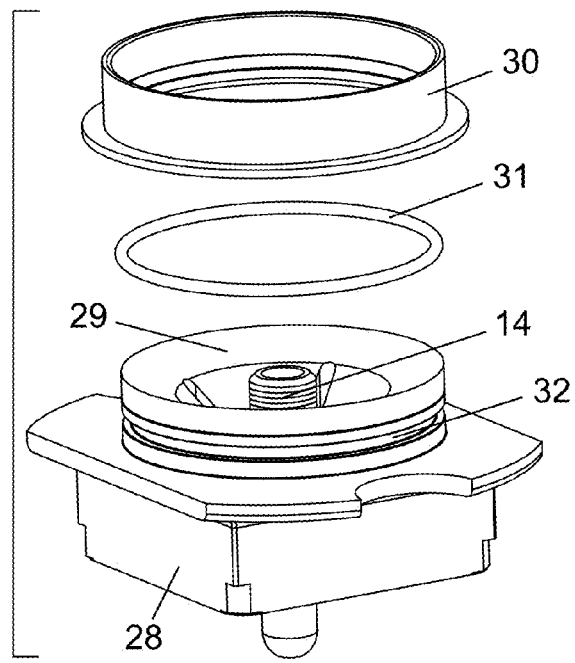
FIG. 5A and FIG. 5B are an assembled and partially exploded view of the four bolt lock housing lamination adapter, a feature of the forced dynamic convection system to be attached to a residual limb in accordance with the present invention.
Figure 5A:
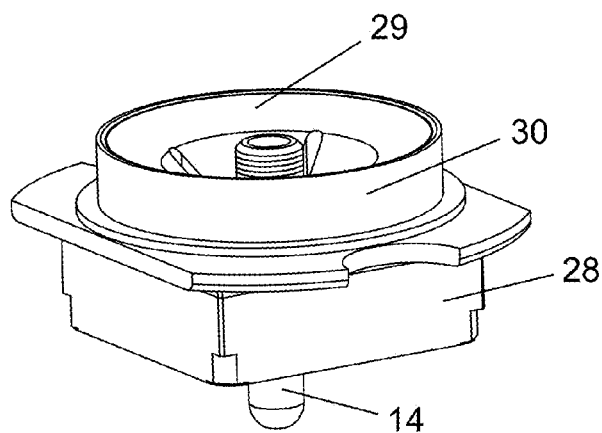

Referring to FIG. 5A and FIG. 5B, a four bolt lock housing lamination adapter 28 is depicted, which fits a commercially available lock mechanism and plunger (not depicted) providing secure suspension between the liner with convection pin and the rigid socket. The four bolt lock housing lamination adapter 28 in lamented into the distal end of a prosthetic rigid socket frame comprising, for example, carbon fiber and epoxy. It has the industry standard six millimeter four bolt pattern that modular artificial limb industry components fit. The hollow convection pin 14, comprising a distal air outflow port, is secured by this lock mechanism and it passes through the housing to engage an O-ring seal in a convection manifold (depicted in FIGS. 6A and 6B). A monolithic funnel 29, has a steep angled central conical channel to guide the convection pin 14 into the lock mechanism. A flexible inner socket retaining ring 30 is to be bonded to a flexible inner socket secured by the rigid socket frame. An O-ring 31 creates an airtight seal between the lock mechanism and the flexible inner socket. An O-ring 31 resides in a gland 32 in the four bolt lock housing lamination adapter 28, and provides a way of securing the flexible liner to the lock mechanism. A flexible inner socket provides patent comfort in an artificial limb as bony prominences can be relieved with socket frame fenestrations. A flexible inner socket allows socket fit modifications; for example, pads between the rigid frame and flexible inner socket can adapt the socket to residuum morphological changes over long term periods of artificial limb use. Creating a flexible inner socket with an airtight seal to the lock mechanism allows airflow from the continuously operating airflow generation device to be directed to the exterior of the convection liner, should that embodiment be desired, as well as provide the opportunity to create a sealed negative gauge pressure environment between the exterior of the liner and the socket frame. Should a flexible inner socket not be prescribed for the artificial limb, a solid spacer can be substituted using O-ring 31 as a method of secure attachment.

Figure 6B:
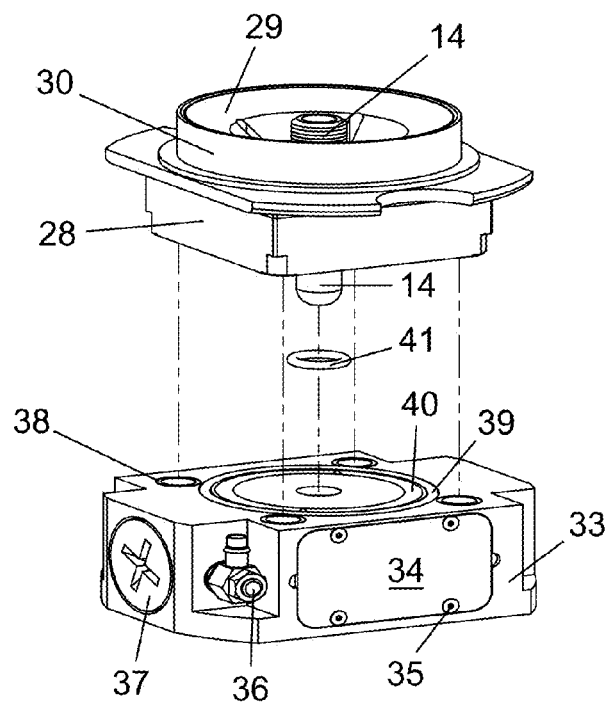
FIG. 6A and FIG. 6B are an anterior isometric assembled and partially exploded view of the four bolt lock housing lamination adapter and convection manifold, which are features of the forced dynamic convection system to be attached to a residual limb in accordance with the present invention.
Figure 6A:
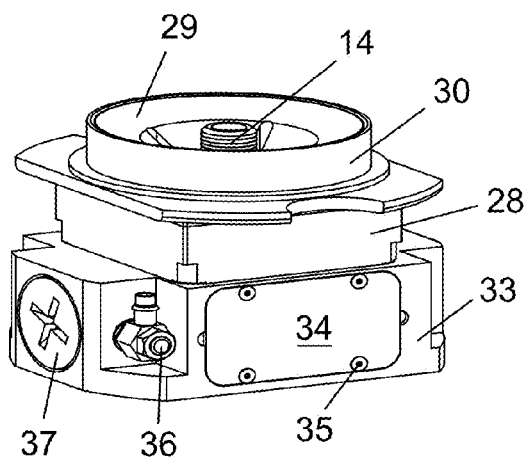

Referring to FIG. 6A and FIG. 6B, the four bolt lock housing lamination adapter 28 with a monolithic funnel 29 and flexible inner socket retaining ring 30 is shown in a potential anterior assembly relationship with the convection manifold housing 33. The convection manifold housing 33 can be universally configured in anterior and posterior placement of ports, plugs and fittings on an artificial limb. As depicted in FIG. 6A, the convection manifold housing 33 has an absorbent housing access plug 37, which holds an absorbent material to extract moisture from the airflow path, which ultimately passes to the continuously operating airflow generation device; a pressure signal O-ring boss rotating barb elbow fitting for tubing 36 allows fluid communication to a pressure transducer; and an optional muffler housing cover plate 34, which is secured by four screws 35. FIG. 6B is a partially exploded view which depicts the top surface of the convection manifold housing 33. There are four load stanchions 38 which bridge between an industry standard pyramid adapter (not depicted) and the four bolt lamination adapter 28, which allows the convection manifold not to bear weight in the system construction. The hollow convection pin 14, which comprises a distal air outflow port, engages an airtight negative gauge pressure O-ring seal 41 housed in an O-ring gland in the convection manifold housing 33, which allows leak proof fluid communication between the inside of the liner, or outside of the liner or a combination of both and the convection manifold housing 33. Should the system embody an optional battery operated electric continuously operating airflow generation device, the convection manifold housing 33 has an exhaust flow annular ring 40 that mates with an annular ring (not depicted) in the four bolt lamination adapter 28 and is bounded by an inner axial O-ring gland (not depicted) in the four bolt lamination adapter 28, and an outer axial O-ring gland 39 in the top surface of the convection manifold housing 33. These two O-rings (not depicted) create an airtight seal along the mating faces of the convection manifold housing 33 and the four bolt lamination adapter 28. The exhaust flow annular ring 40 directs exhaust flow to a series of muffler baffles (not depicted) on either side of the convection manifold, located behind the muffler housing cover plate 34. The muffler baffles effectively reduce the noise of a battery operated continuously operating negative gauge pressure pump, should such an optional embodiment be configured.

Figure 7A:
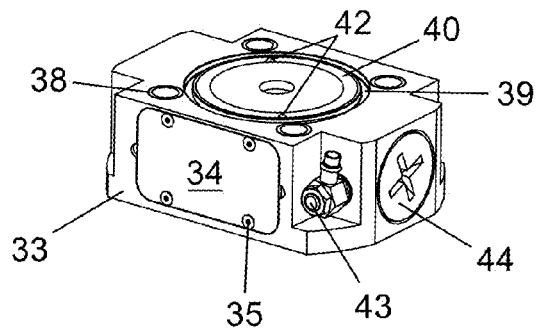
FIG. 7A, FIG. 7B, and FIG. 7C are a posterior isometric assembled view, lengthwise cross-section and a partially exploded view of the convection manifold, which is a feature of the forced dynamic convection system to be attached to a residual limb in accordance with the present invention.
Figure 7B:
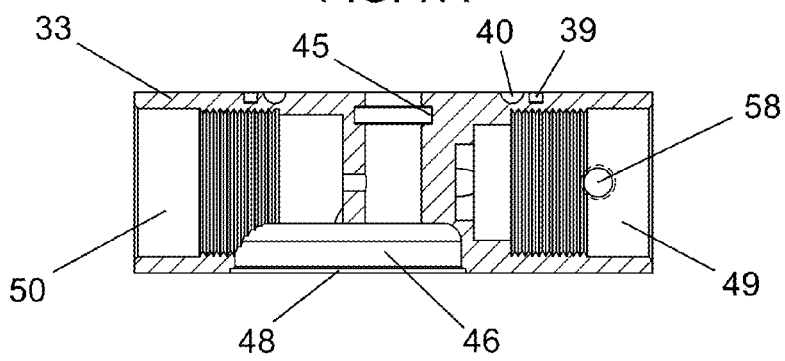
Figure 7C:
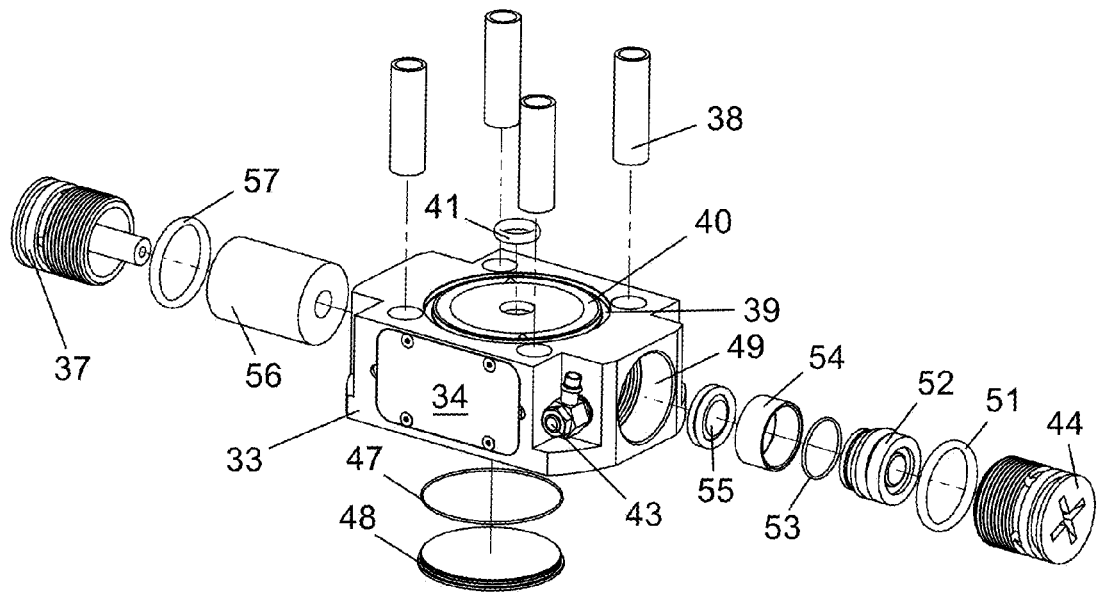

Referring to FIG. 7A, FIG. 7B and FIG. 7C, the convection manifold housing 33 is shown in a potential assembly of constituent parts in a posterior isometric view, in a lengthwise cross-section and in a partially exploded view respectively. The convection manifold housing 33 can be universally configured in anterior and/or posterior placement of ports, plugs and fittings on an artificial limb. In this depiction one of the potentially two, airflow convection manifold O-ring boss rotating barb elbow fitting for flexible tubing 43 directs airflow to the continuously operating airflow generation device. A filter housing and spring and poppet leak prevention device threaded plug retainer 44 is accessible from the posterior of the convection manifold housing 33. It creates an airtight seal to the convection manifold housing 33 through an O-ring 51 retained in an O-ring gland in the filter housing and spring and poppet leak prevention device threaded plug retainer 44, which seals against the sealing area 49 in the convection manifold housing 33. Airflow travels down a hollow convection pin which is sealed by an O-ring 41, which is retained in an O-ring gland 45, into a moisture reservoir 46, which is sealed by an O-ring 47 retained in an O-ring gland in the cover plate 48. After depositing moisture droplets into the reservoir 46, the airflow travels up around the exposed absorbent material 56, which is retained by the absorbent housing threaded access plug 37, which creates an airtight seal to the convection manifold housing 33 through an O-ring 57 retained in an O-ring gland in the absorbent housing threaded access plug 37, which seals against the sealing area 50 in the convection manifold housing 33 and also provides transducer pressure signal communication through the center of the absorbent housing threaded access plug via holes in an annular ring to a pressure signal O-ring boss rotating barb elbow fitting for flexible tubing, exiting the convection manifold housing 33 to a transducer on a circuit board. The air then travels to a filter complex 55, comprised of two soft O-rings bonded to a stainless steel pleated filter, which fits inside a stainless steel retainer 54, and creates a direct sealed airflow path to a spring and poppet leak prevention device 52, which is sealed to retainer 54 by O-ring 53. The spring and poppet leak prevention device 52 has a side sealing O-ring (not depicted) retained in a gland in its housing and fits with an airtight seal inside the filter housing and spring and poppet leak prevention device threaded plug retainer 44. This allows filtered air to pass through holes in an annular ring in the filter housing and spring and poppet leak prevention device threaded plug retainer, sealed from environmental air by O-ring 51 sealed to the sealing surface 49 of the convection manifold housing 33 and out one of the threaded exit holes 58 to one of the potentially two convection manifold airflow O-ring boss rotating barb elbow fitting for flexible tubing 43.

There are four load stanchions 38, which allow the convection manifold not to bear weight. Four high strength forty millimeter long screws in an industry standard M6×1 thread and pitch, pass through these stanchions and secure an industry standard pyramid adapter (not depicted) and the four bolt lamination adapter. The exhaust flow path from a potentially battery operated continuously operating airflow generating device may require a muffler to address noise issues during operation. The exhaust flow is potentially directed through the convection manifold in an isolated fashion from the airflow generation pathways of the forced dynamic convection system. The exhaust airflow travels through two separate series of baffles located under the muffler housing cover plate 34, which is secured by four screws 35, exhaust flow travels along matching annular rings in the four bolt lamination adapter (not depicted) and in the convection manifold 40, which is sealed from environmental air to prevent noise by an O-ring in an axial gland 39 and is also bounded by an inner axial O-ring gland in the four bolt lamination adapter. Exhaust flow is directed to the two separate series of baffles through two downward flow paths 42, which can be arranged in various configurations in directing the flow of the exhaust relative to the baffles.

It should be noted that, for convenience, both the absorbent housing threaded access plug 37 and the filter housing and spring and poppet leak prevention device threaded plug retainer 44 can be removed from the convection manifold with various coins, e.g. of U.S. currency.

Figure 8:
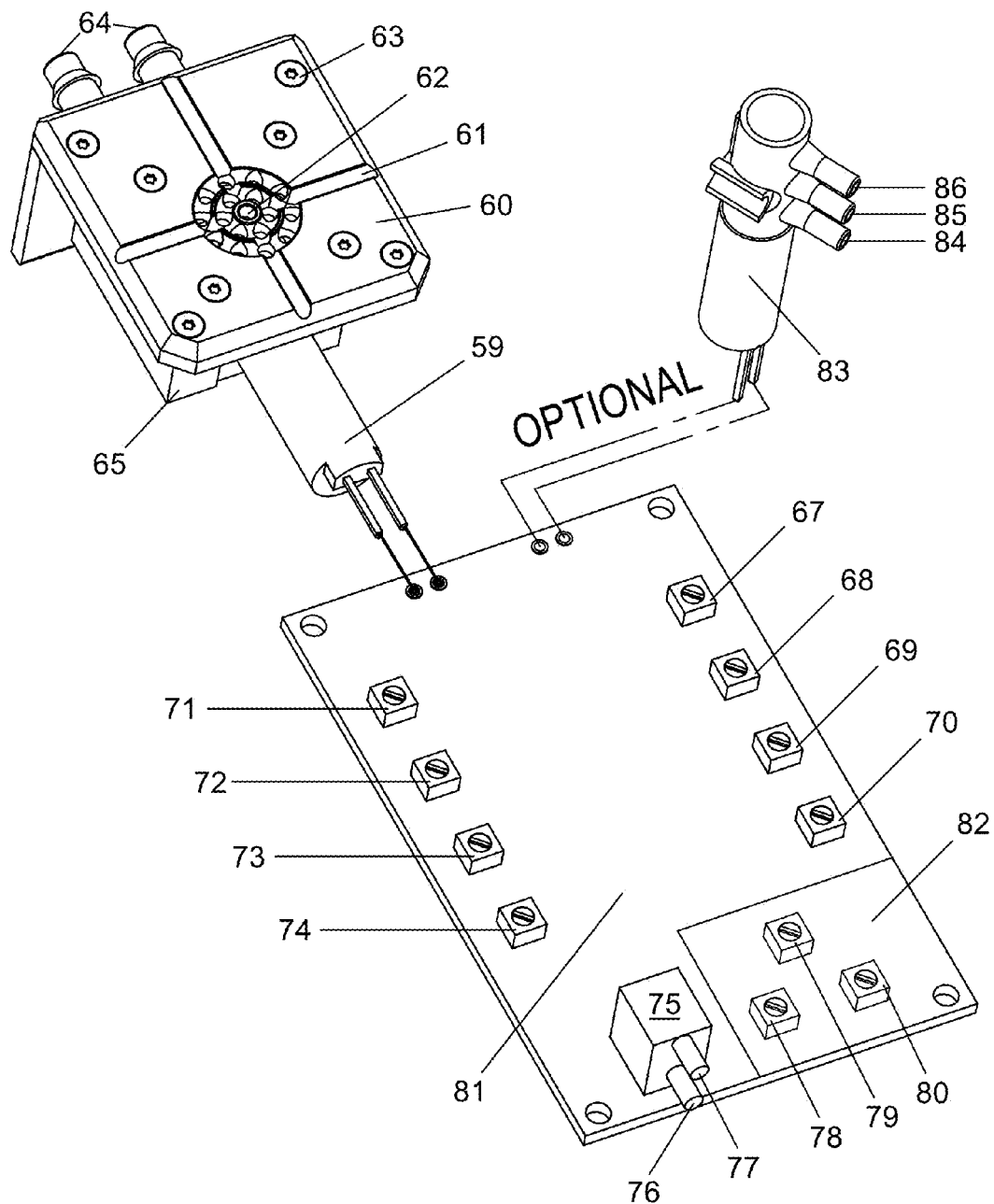
FIG. 8 is schematic representation of the convection control system's circuit board and electromechanical binary airflow proportioning devices, which are features of the forced dynamic convection system to be attached to a residual limb in accordance with the present invention.

Referring to FIG. 8, depicted is a circuit board constituting the convection control system 81. It contains circuitry 82 that adjusts the attributes of a continuously operating battery operated airflow generation device, as well as a body powered airflow generation device. It also contains circuitry of the rising edge triggered negative gauge pressure regulation device controlling an electromechanical binary airflow proportioning device 59.

The circuit board 81 plugs into, with surface mount header pins, the electronic circuits of the Dynamic Air Exchange System. Although it could be configured as a standalone board, for example, in a potential configuration that solely uses a body powered airflow generation device, as depicted, derives its power from the common battery power source of the circuit boards in the Dynamic Air Exchange System and processes signals and modifies the characteristics and behavior of both system components and electronic designs.

The electronic circuits that comprise the existing Dynamic Air Exchange Systems can be described as falling edge pressure regulation. A sealed environment between the residuum and the liner maintains a static sealed negative gauge pressure. An airflow initiating device is opened by user command resulting in lessening of the negative gauge pressure and once a set pressure threshold is crossed by the falling negative gauge pressure level, the control circuitry acts to increase the negative gauge pressure by operating an electric airflow generation device in the sealed environment. The present invention controls rising edge negative gauge pressure. A rising negative gauge pressure would be illustrated by the decreasing absolute pressure of 25.4 mmHg to 152.4 mmHg. A rising edge trigger is a pressure threshold event resulting from rising negative gauge pressure. For example, upon reaching a set pressure threshold, a rising edge triggered negative gauge pressure regulation device, which may comprise an electromechanical binary airflow proportioning device (solenoid) 59 and associated control circuit 81, will open an electromechanical binary airflow proportioning device, opening an air flow path to the atmosphere. This acts to regulate the pressure in a sealed environment between the limb and liner or the liner and socket or a combination of both. The airflow generation device in this invention is preferably continuously operating and the negative gauge pressure is regulated by the action of an electromechanical binary airflow proportioning device 59, or a mechanical spring and poppet mechanism or an one-piece elastomeric valve, relieving the increasing negative gauge pressure build up. To keep a continuously operating airflow generation device that is ported to the inside of the liner from conflicting with the falling edge regulations systems of the existing Dynamic Air Exchange System, a non-symmetrical low pass signal filter is activated during dynamic convection. The filter has a long time constant for decreasing negative gauge pressure and a fast time constant for increasing negative gauge pressure, which allows smart filtering of the falling edge activated, battery operated, pump and associated control circuit to function optimally.

The convection control system 81 employs regulated cyclical differential pressure airflow through continuously operating airflow generation device and a rising edge triggered negative gauge pressure regulation device. Airflow is directed inside or outside a limb conformable convection suspension liner, or a combination of both flow paths, through various system architecture configurations, which provides thermal energy transfer from within an artificial limb to the ambient atmosphere. This convection occurs due to temperature difference between the inside of the artificial limb and the ambient atmosphere. The energy transfer of forced dynamic convection mitigates excessive thermal buildup, which in a linear fashion mitigates the amount of perspiration generated.

Efficient energy transfer by forced dynamic convection is achieved by constant airflow. When a negative gauge pressure pump is employed to move air by creating a pressure differential and configured to be constantly operating, it is considered a continuous airflow generation device. A continuous airflow generation device comprises either a battery operated design, controlled by unique circuitry 82 to operate in a quiet, energy efficient manner, or a body powered mechanical design, which are specifically configured for artificial limbs and currently provided by various device manufacturers. These mechanical negative gauge pressure pumps are either actuated by body weight or the dynamics of ambulation.

The electromechanical binary airflow proportioning device 59 is retained in a receiving block 65, with a cover plate 60 that has occlusion prevention grooves 61 leading into air inlet holes 62 down to a filter (not depicted) which protects the operating mechanism of the electromechanical binary airflow proportioning device 59. There are eight screws 63, the outermost four retain the assembled housing in the rigid socket over-mold, and the innermost four screws retain the cover plate to the receiving block 65, removal of these screws allows access to the inlet air filter. Depicted are two of at least one electromechanical binary airflow proportioning O-ring boss straight barb fittings for tubing 64 could be variously attached to inlet air channel tubing in fluid communication with inlet air channel caps that affix to the proximal air channel inflow port with occlusion preventing flange (21, FIG. 4B) of the convection liner or to a similar inflow port mounted in the rigid socket frame or the sealed flexible inner socket. The receiving block can be configured up to four electromechanical binary airflow proportioning O-ring boss barb fittings for tubing, allowing various system configurations.

The circuit is designed to be potentially configured to control two electromechanical binary airflow proportioning devices working in tandem to maintain an adjustable negative gauge pressure in two sealed environments, e.g. one dynamically and one statically. The addition of the optional airflow path directing electromechanical binary airflow proportioning device 83 allows the negative gauge pressure of the continuous airflow generation device to be coupled and decoupled from, for example, the sealed environment between the outside of the convection liner and the interior of the rigid socket frame or flexible inner socket. The pressure transducer 75 is in communication with the ambient environment as a reference pressure through port 76 and can be directed to any sealed environment in an artificial limb through port 77 to quantize the differential gauge pressure. (Span adjustment 74 allows for full scale adjustment of the desired system negative gauge pressure level adjustment. Negative gauge pressure sensor zero adjustment 73 adjusts for irregularities in the manufacture of the pressure sensor 75.) If the transducer were to be ported to a sealed environment on the outside of the liner and inside the rigid socket, an upper negative gauge pressure threshold adjustment 70 and a lower negative gauge pressure threshold adjustment 69 establishes the operational negative gauge pressure band of this environment's static environment, whilst working in tandem with the rising edge negative gauge pressure regulating device's electromechanical binary airflow proportioning device 59 in the dynamic environment inside of the convection liner.

A circuit operational cycle will now be described; a constantly operating body powered pump or battery operated pump generates airflow in a forced convection system configured with the optional second electromechanical binary airflow proportioning device 83. The optional airflow path directing electromechanical binary airflow proportioning device 83 acts to control airflow (coupling—decoupling) to either the outside or inside of the liner. The continuous airflow generation device is connected to the common middle port 85, the top port 86 is in fluid communication with the sealed environment between the residuum and the liner, and the bottom port 84 is in fluid communication with the sealed or unsealed environment between the outside of the convection liner and the inside of the rigid socket frame, or flexible inner socket. The other electromechanical binary airflow proportioning device 59 acts as a rising edge triggered negative gauge pressure regulating device, which allows environmental air into any sealed environment in the artificial limb, in this example it will be the inside of the convection liner. The two of the at least one electromechanical binary airflow proportioning O-ring boss straight barb fitting for tubing 64 are attached to inlet air channel tubing in fluid communication with caps that affix to the proximal air channel inflow port with occlusion preventing flange of the convection liner. The receiving block 65 can be optionally configured for one to four electromechanical binary airflow proportioning device O-ring boss straight barb fittings for tubing depending on the system configuration.

Initially, the cycle starts off where the airflow and negative gauge pressure is directed through the common port 85 on through the open bottom port 84 to the sealed environment of outside of the liner and the inside of the rigid socket (or flexible socket), whose upper threshold of seventy-six mmHg has been adjusted by potentiometer 70 and the lower threshold adjusted by potentiometer 69 to a value of thirty-eight mmHg. Once the pressure threshold of seventy-six mmHg has been achieved by the airflow generating device operating in a sealed environment, the optional air flow path directing electromechanical binary airflow proportioning device 83 decouples the airflow and negative gauge pressure from the inner socket, outside of the liner environment and couples the continuously operating airflow generation device to the inside of the liner. Inside the sealed inner convection liner environment, a rising edge threshold is adjusted by potentiometer 68 to a negative gauge pressure level of eighty-nine mmHg and can be further fine-tuned with both a delay in opening adjustment 67 and a delay in closing adjustment 71, which effectively sets the hysteresis band of the system. Once the eighty-nine mmHg threshold is crossed by the continuously operating body powered airflow generation device, the electromechanical binary airflow proportioning device opens and closes, regulating the negative gauge pressure through timed cyclical differential pressure airflow. The pressure transducer 75 is in fluid communication with the sealed environment of the outside of the convection liner and inside the rigid socket through port 77. If the pressure drops below the established lower threshold of thirty-eight mmHg, the airflow path directing optional electromechanical binary airflow proportioning device 83 decouples the continuously operating negative gauge pressure generating device from the inside of the liner and directs it back to the outside of the liner (airflow via bottom port 84) until the set upper threshold of seventy-six mmHg is achieved and then the airflow is coupled back to the inside of the liner (airflow via top port 86), completing the cycle. It should be noted that a negative gauge pressure level of seventy-six mmHg in the sealed environment between the exterior of the liner and the inside of the socket is a negative gauge pressure level achievable by industry standard auto expulsion modular valves used in typical suction socket suspension designs.

An over-band safety threshold 72 adjustment is set at the highest level of negative gauge pressure the residuum can directly tolerate for a brief amount of time. This setting is not intended to be a normal operational setting of the system; it is a result of some system component failure. A potential setting might be 203 mmHg. This threshold will open the electromechanical binary airflow proportioning device 59, irrespective of the state of the coupling decoupling electromechanical binary airflow proportioning device 83, allowing environmental air into sealed environment preventing negative gauge pressure from rising above this over-band safety threshold level. There are numerous potential configurations of the convection control system 81. It can be configured to use only one electromechanical binary airflow proportioning device. The circuit is robust enough to reliably operate multiple electromechanical binary airflow proportioning devices configured in parallel. Airflow then could be directed to a surge reservoir so that increased velocity of forced dynamic convection can be achieved through a configuration those skilled in art will appreciate. The advantage of decoupling afforded by the dual binary airflow proportioning devices is safety. If for some reason, the safety threshold, adjusted by potentiometer 72 is crossed (e.g. a system malfunction), the continuous airflow can be isolated away from the critical environment of the residuum inside of the liner.

The forced convection circuit board allows the battery operated negative gauge pressure generating device of the existing Dynamic Air Exchange System to be operated as a continuously operating airflow generation device. When in forced dynamic convection mode, a unique motor velocity is controlled by potentiometer 78, a unique negative gauge pressure level is set by potentiometer 79 and a unique hysteresis band is adjusted by potentiometer 80. These settings are only are active during forced convection. These adjustable settings are to optimize system performance, minimize device noise and conserve battery life.

Referring to FIG. 9A, FIG. 9B and FIG. 9C, illustrated are various views of an alternate embodiment of the rising edge triggered negative gauge pressure regulation device. A mechanical binary airflow proportioning design 87, which comprises a proximal air channel inflow port with occlusion preventing flange 21 from the existing Dynamic Air Exchange System design, a one-piece elastomeric valve 88, an O-ring 89, retained in a gland in the detachable cap inlet air channel cap 91 with a filter 90. This mechanical binary airflow proportioning design 91 operates without the need of a control circuit or battery power. Pressure is regulated by the configuration and action of the one-piece elastomeric valve 88, which is fitted into a recessed crown of the proximal air channel inflow port with occlusion preventing flange 21. The valve opens on increasing negative gauge pressure and closes on decreasing negative gauge pressure. A filter 90 is connected to a detachable inlet air channel cap 91 which seals with an internal O-ring 88, to create an airtight seal. A mechanical spring and poppet or valve mechanism is an alternative potential construction and would act similarly to the one-piece elastomeric valve.

A simplified embodiment of the forced dynamic convection system will now be described using a mechanical binary airflow proportioning design: A socket employing sealed suction suspension is outfitted with a body powered airflow generation device connected to the convection manifold (FIGS. 7A-C); a single mechanical binary airflow proportioning device 87 is attached to the proximal aspect of a rigid socket. A convection liner outfitted with a hollow convection pin inserted into an exterior convection pin threaded adapter (FIGS. 3A-B) so that airflow is directed to the outside of the liner. With each step, airflow enters the socket, travels along the outside of the convection liner and enters the convection manifold through the convection pin comprising a distal air outflow port and out through the body powered negative gauge pressure airflow generation device, achieving thermal transfer with the ambient atmosphere.

An alternate construction would have the mechanical binary airflow proportioning design 87 attached to the convection liner. A body powered airflow generation device could be connected to the convection manifold (FIGS. 7A-C): a single mechanical binary airflow proportioning device is attached to the proximal aspect of the convection liner which has a distal air outflow port with occlusion preventing flange (FIGS. 4A-B). A multi-ply surface area multiplying textile layer with airflow seal covers the residuum and the convection liner has interior convection pin adapter (FIGS. 13A-B), a hollow convection pin, allowing airflow to be directed only to the inside of the liner. With each step, airflow enters the sealed environment between the residuum and liner, travels along the inside of the convection liner through the textile layer the liner's airflow grooves and enters the convection manifold through the hollow convection pin comprising a distal air outflow port and out through the body powered negative gauge pressure airflow generation device, achieving thermal transfer with the ambient atmosphere. Experience has shown that a filter 90 has helped with the reliability of practical reductions to practice of this embodiment with either an elastomeric one piece valve 88 or a spring and poppet configuration (not depicted) but an electromechanical binary airflow proportioning configuration with an electromechanical airflow generating device has proven to be a more reliable fail-safe design.

Figure 10:
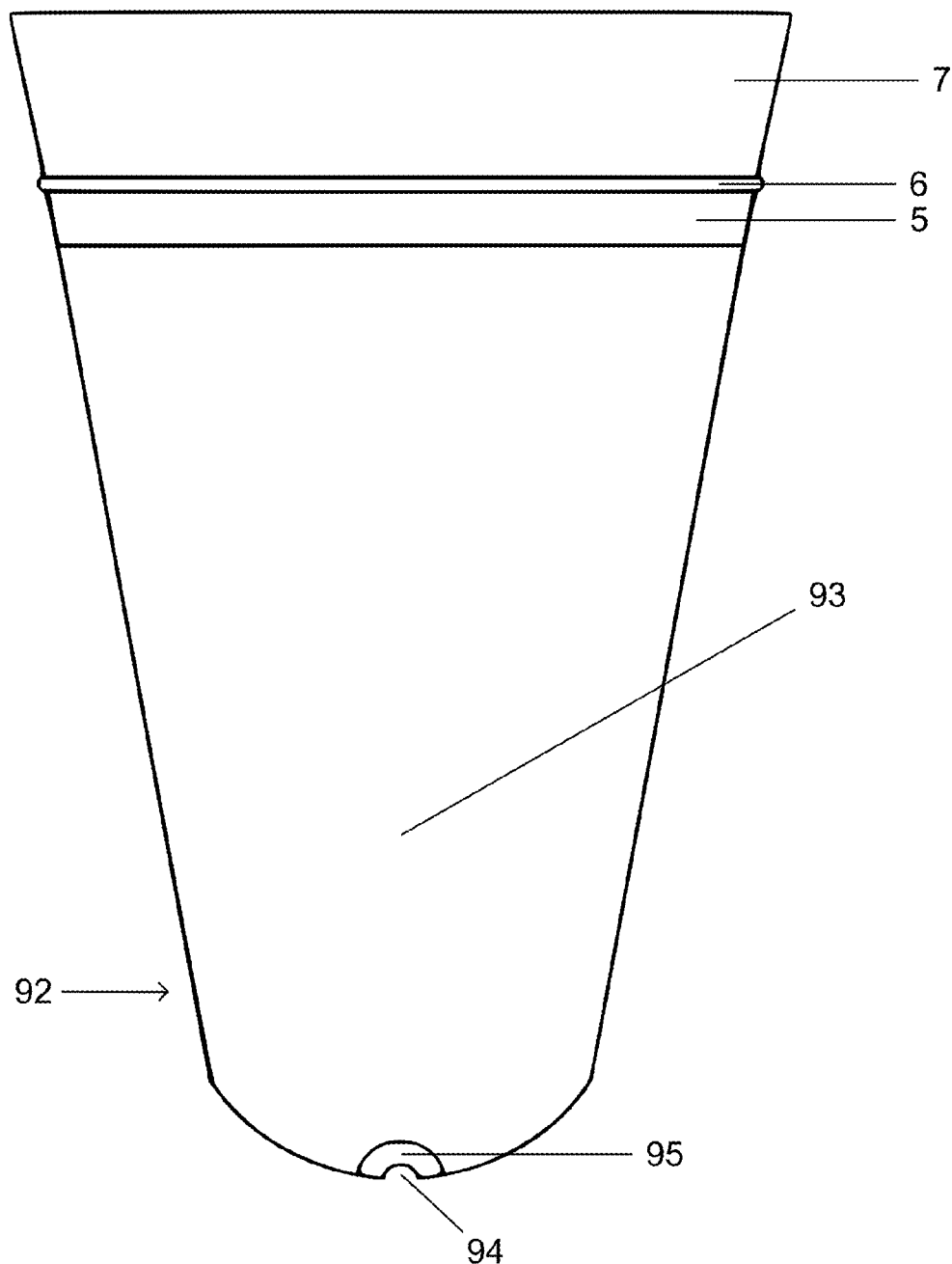
FIG. 10 is an anterior view of the exterior liner surface area multiplying textile layer with proximal airflow seal to be attached to a residual limb liner in accordance with the present invention.

Referring initially to FIG. 10, an exterior liner surface area multiplying textile layer with proximal airflow seal 92, which comprises a monolithic textile layer 93, and optional distal hole 94 for a convection pin, an impregnated anti-fraying annular region 95, a laminate transition area 5, a raised annular ring 6, and an airflow seal 7 will now be described.

The exterior liner surface area multiplying textile layer with proximal airflow seal 92 is intended to be donned over the convection limb conformable liner to improve its airflow capacity and allow an industry standard sealed suction suspension socket design to be created. A sealed suction suspension socket might typically have negative gauge pressure level of seventy-six mmHg, which is a pressure level that has been achievable in the artificial limb industry for decades. The exterior liner surface area multiplying textile layer with proximal airflow seal 92 surrounds at least a portion of the exterior surface of the convection liner and defines a sealed negative gauge pressure environment between the exterior liner and the socket, which facilitates airflow in an industry standard suction suspended socket design. The airflow seal 7 of the surface area multiplying textile layer 93 includes a gently tapered laminate transition area 5, where the fibers of the textile are adherently intertwined with silicone and terminate at the raised annular ring 6. The annular ring 6 and proximal seal area 7 are devoid of textile fibers, which effectively seals both pressure and airflow between the exterior of the convection liner and the interior of the artificial limb socket. As such, the airflow seal 7 is preferably an impervious seal. Although monolithic in structure, the exterior textile layer is also continuously cavitated, which means the volume of the textile layer comprises interconnected cavities which are continuous with the exterior of the material, aiding airflow and convection.

The lock housing depicted in FIG. 5A and FIG. 5B and the convection manifold depicted in FIG. 7A-C allows a hollow convection pin to be used, while maintaining an airtight seal in the socket. The proximal seal area 7 of the exterior liner surface area multiplying textile layer 92 creates an airtight seal between the exterior liner and the prosthetic socket. A rising edge binary airflow proportioning device (FIG. 8 and FIG. 9A-C) would be attached to the socket (or flexible inner socket) aligned with the level of the textile layer 93 on the exterior liner, so that a cyclical differential pressure airflow into the sealed environment between the exterior liner and the socket will achieve forced dynamic airflow convection while maintaining the seal necessary for a suction suspension socket. Regarding the hollow convection pin, it is a redundant suspension mechanism as well as a distal convection channel. The distal hole 94 in the textile layer 93 is reinforced with a flat elastomeric impregnated annular region 95 to prevent fraying of the knitted yarns of the textile layer 93.

Figure 11A:
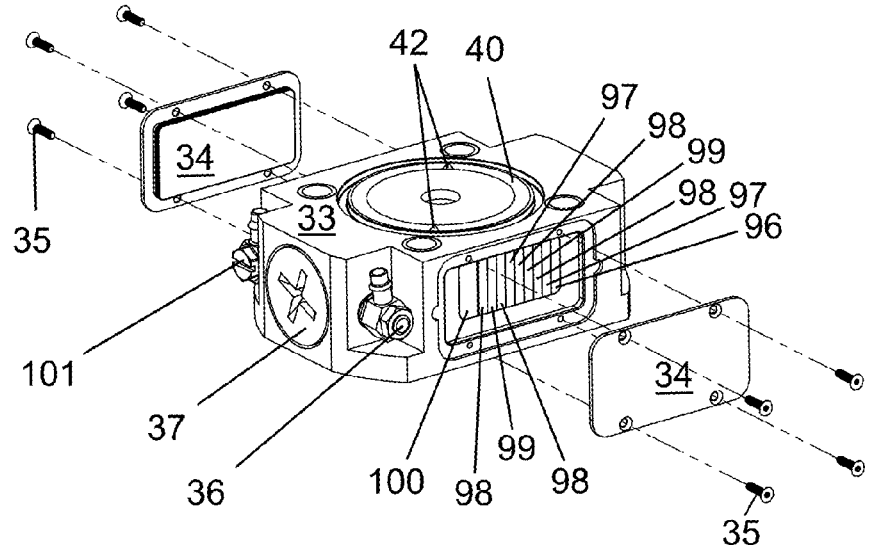
FIG. 11A and FIG. 11B are an anterior isometric partially assembled view, and a exploded view of the muffler assembly in the convection manifold, which is a feature of the forced dynamic convection system to be attached to a residual limb in accordance with the present invention.
Figure 11B:
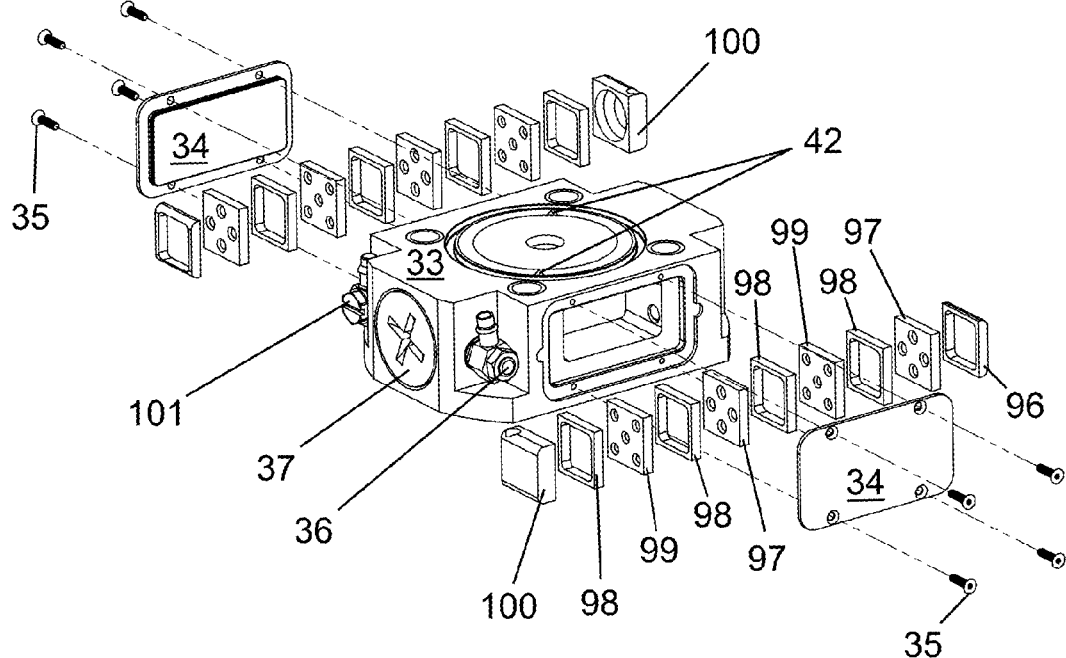

Referring to FIGS. 11A and 11B, depicted is an potential anterior isometric and exploded view of the convection manifold housing 33, with the muffler housing cover plate 34 and screws 35 removed to reveal the location and order of the exhaust air baffles 97, 99, spacers 96, 98 and transition plates 100. The convection manifold housing 33 and muffler flow paths can be universally configured in anterior and/or posterior placement of ports, plugs and fittings on an artificial limb. The exhaust air baffles are configured with either four flow holes 97 or five flow holes that are countersunk to reduce airflow resistance and are of a sufficient sized diameter to minimize backflow pressure to a potentially configured battery operated negative gauge pressure airflow generating device. Forced dynamic convection employs regulated cyclical differential pressure airflow, which necessitates a continuously operating airflow generation device (and a rising edge triggered negative gauge pressure regulation device). A continuously operating battery powered negative gauge airflow generation device necessitates a muffler on its exhaust side to minimize its operational noise.

Depicted for reference, a pressure signal O-ring boss rotating barb elbow fitting for tubing 36 allows fluid communication to a control circuit pressure transducer. The absorbent housing accesses plug 37, which holds an absorbent material to extract moisture from the airflow path is also depicted. It should be noted that the airflow and exhaust flow paths in the convection manifold design are isolated from each other.

There are two rows of ten baffles on either side of the convection manifold. Exhaust air from the negative gauge airflow generating device enters from a face sealing elbow barb 101 on the anterior aspect of the convection manifold, goes through various spacers and baffles until it reaches a transition plate 100 which directs the exhaust flow upward to the top of the convection manifold, via one of the two connecting holes 42 and around through an annular ring 40, and back down into the opposite side of baffles through an identical transition plate 100, which directs the exhaust flow to the baffles and spaces on the other side of the convection manifold, making a "Z" flow path. A "U" flow path is an optional configuration. Airflow exits out through the posterior of the convection manifold and sound waves can be further attenuated with a breather fitting, additional tubing or holes through the muffler cover plate 34.

Figure 12:
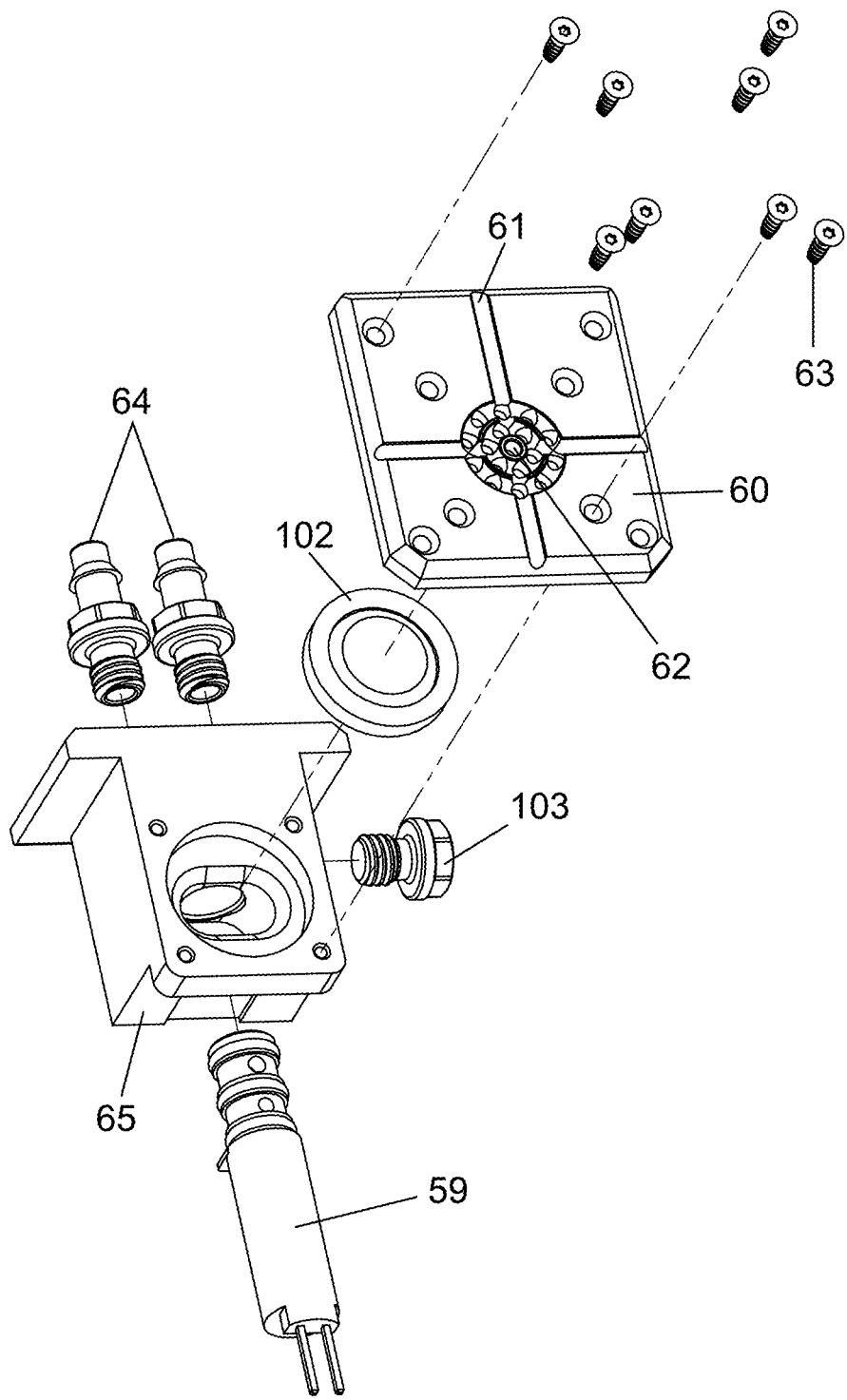
FIG. 12 is an exploded view of the electromechanical binary airflow proportioning housing which is a feature of the forced dynamic convection system to be attached to a residual limb in accordance with the present invention.

Referring to FIG. 12, an exploded view of the electromechanical binary airflow proportioning housing is depicted.

The electromechanical binary airflow proportioning device 59 is to be mounted in a receiving block 65, with a cover plate 60 that has occlusion prevention grooves 61 leading into air inlet holes 62. A filter 102 protects the operating mechanism of the electromechanical binary airflow proportioning device 59 from debris. There are eight screws 63, the outermost four retain the electromechanical binary airflow proportioning device's housing in the rigid socket over-mold, and the innermost four screws retain the cover plate to the receiving block 65, removal of these screws allows access to the inlet air filter. Two of at least one electromechanical binary airflow proportioning O-ring boss straight barb fitting for tubing 64 could be variously attached to inlet air channel tubing in fluid communication with inlet air channel caps that affix to the proximal air channel inflow port with occlusion preventing flange (21, FIG. 4B) of the convection liner or to a similar inflow port mounted in the rigid socket frame or the sealed flexible inner socket. A block O-ring boss plug 103 seals an optional flow path, forward of the operating mechanism of the electromechanical binary airflow proportioning device 59, to allow multiple solenoids to be in fluid communication with each other. The receiving block can be ultimately configured for four electromechanical binary airflow proportioning O-ring boss straight barb fitting for tubing 64 depending on the system configuration.

Figure 13A:
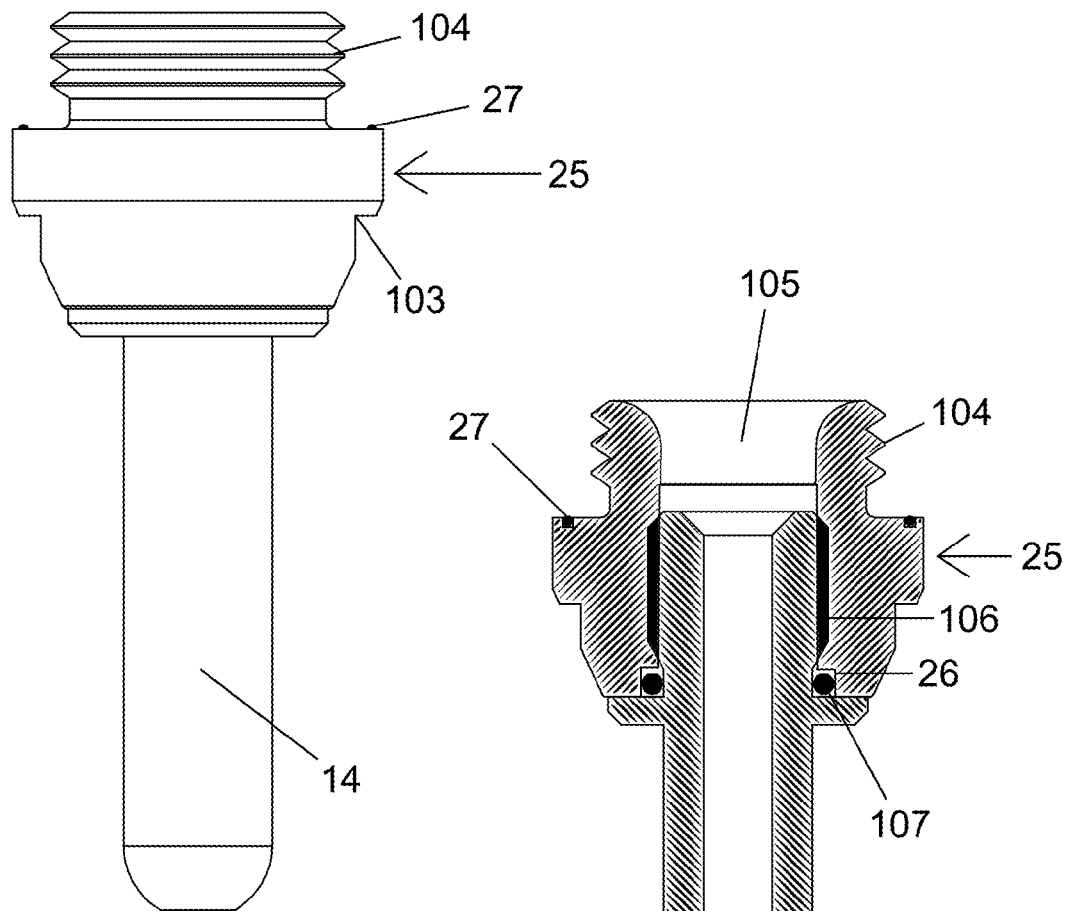
FIGS. 13A and 13B are an anterior view and a cross-sectional view of the exterior convection pin adapter in accordance with another embodiment and a feature of the convection artificial limb liner to be attached to a residual limb in accordance with the present invention.
Figure 13B:
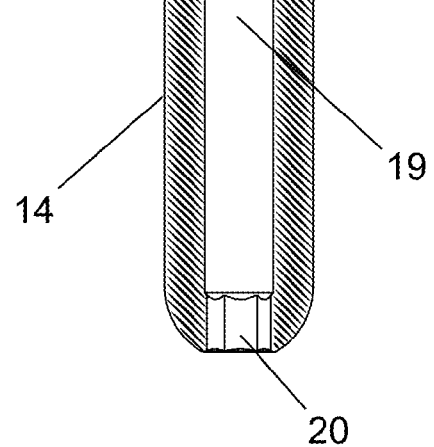

Referring to FIGS. 13A and 13B, a removable interior convection pin adapter 25 is depicted with an interfacing hollow convection pin 14, which comprises a central convection channel 105, O-ring axial seal 27 and O-ring sealing gland surface 26 to the convection pin 14, threads 106 to receive an interfacing convection pin 14 and threads 104 for installation into an umbrella allowing attachment to the convection liner. Wrench flats 103 allow secure installation as well as removal for alternately configured convection pin threaded adapters, which can change the functionality of the system. The hollow convection pin 14 has a broached distal region 20 to receive an installation tool for interfacing with the interior convection pin adapter 25 as well as provide an airtight thread seal with an O-ring 107. In the depicted embodiment, this interior convection pin adapter 25 allows forced convection on the inside of the convection liner by the flow of air over the interior of the convection liner and its interior convection channels as well as through the residuum donned tapering textile layer with proximal airflow seal, through a central convection channel 105 and then travels down the distal convection channel 19 of the hollow convection pin 14, into a convection manifold and ultimately into and expelled from the continuously operating airflow generation device of the convection control system.

Figure 14A:
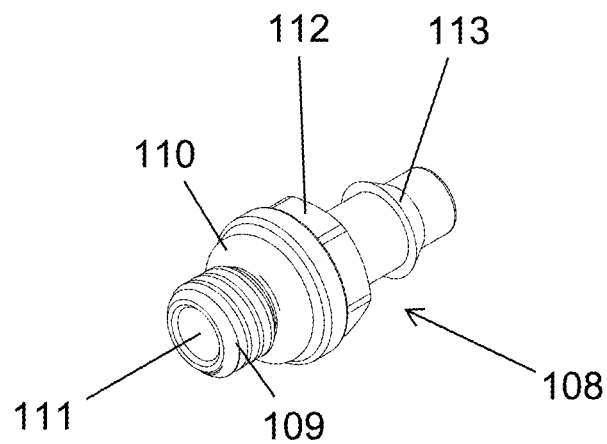
FIGS. 14A and 14B are an isometric assembled and exploded view of a convection O-ring boss straight barb fitting for tubing, which is a feature of the various components of the dynamic convection system to be attached to a residual limb in accordance with the present invention.
Figure 14B:
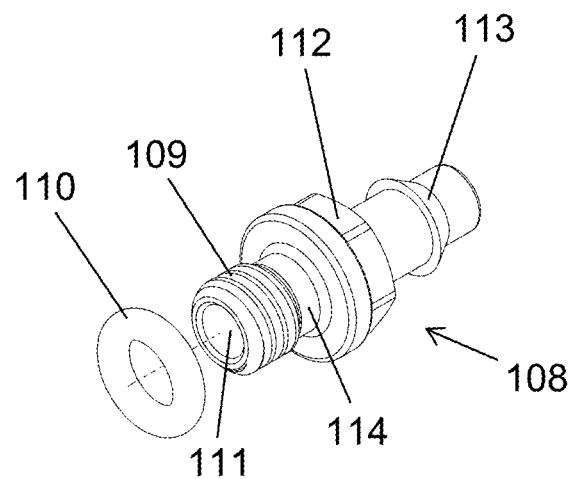

Depicted in FIG. 14A and FIG. 14B is a convection O-ring boss straight barb fitting for tubing 108, which comprises a tubular post and barb to secure tubing 113, a hexagonal section 112 to receive an installation tool, an O-ring sealing gland surface gland 114, and O-ring 110, mounting threads 109 for various interfacing installations and a central air passageway 111. In some configurations air flows through a central air passageway configured through its axial center 111 similar to industry standard barb fitting designs for flexible tubing and in some embodiments, internal geometry is removed so that it functions as a solid plug. Flexible tubing is inserted over the projecting tubular post and barb 113 and securely retained and sealed by its design configuration. Most barb fittings for tubing employ an axial sealing O-ring to seal along the mating surfaces of the barb and the installation. The problem with such a seal, commonly referred to as a face seal, is that slight over torqueing of a standard barb fitting into soft materials, for example plastic, can easily deform the sealing face resulting in negative gauge pressure leaks. This depicted configuration solves the problem by providing a design where the O-ring 110 seals to a sealing surface provided below the surface of the face of the installation, which is recessed and protected from damage, resulting in a leak tight connection. Boss is a descriptive term employed for this design; the threaded area 109 plus the O-ring sealing gland surface 114 is longer than a typical barb fitting and in certain reductions to practice a boss, or a projection above the surface of the installation is thusly required. In this dynamic convection system specification, barb fittings for tubing are numbered uniquely to aid in the description of their respective airflow direction, function and or ports.

Figure 15A:
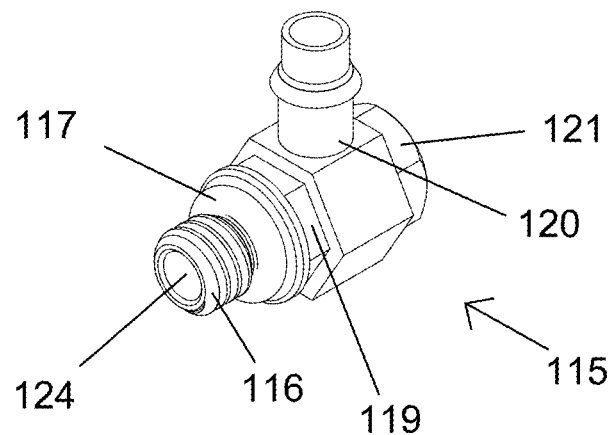
FIGS. 15A and 15B are an isometric assembled and exploded view of a convection O-ring boss rotating barb elbow for tubing, which is a feature of the various components of the dynamic convection system to be attached to a residual limb in accordance with the present invention.
Figure 15B:
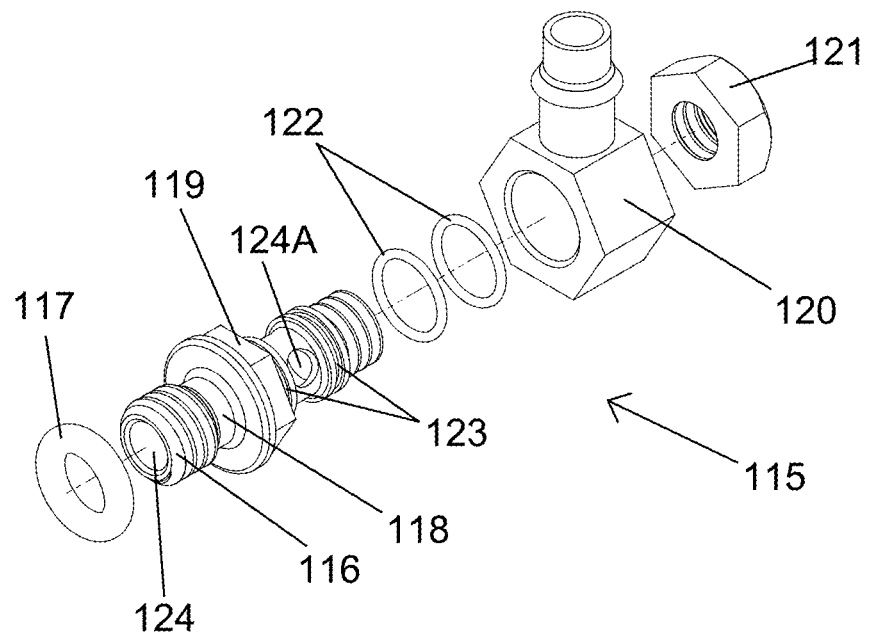

Referring to FIG. 15A and FIG. 15B, depicted is a convection O-ring boss rotating barb elbow for tubing 115, which comprises a hexagonal rotating housing with tubular post and barb 120 to receive and secure tubing, an O-ring sealing gland surface gland 118, and O-ring 117, mounting threads 116 for various interfacing installations and an air passageway 124, which is in fluid communication with the hexagonal rotating housing with tubular post and barb 120, a retaining nut 121, a hexagonal region 119 to receive an installation tool, two O-rings 122, retained in glands 123 to seal the hexagonal rotating housing with tubular post and barb 120 and the airflow transition holes 124A. In a dynamic convection system, continual mass airflow may be preferred, this design is optimized to minimize airflow resistance via a plurality of airflow transition holes 124A, which directs airflow in the O-ring 122 sealed internal chamber of the rotating barb housing, transitioning the flow of air ninety degrees. An O-ring 117 seals to a sealing surface below the surface of the face of the installation, which is recessed and protected from damage, resulting in a leak tight connection. Boss is a descriptive term employed for this design; the threaded area 116 plus the O-ring sealing gland surface 118 is longer than a typical barb fitting and in certain reductions to practice a boss, or a projection above the surface of the installation is thusly required. In this dynamic convection system specification, O-ring boss rotating barb elbows for tubing are numbered uniquely to aid in the description of their respective airflow direction, function and or ports.

Figure 16:
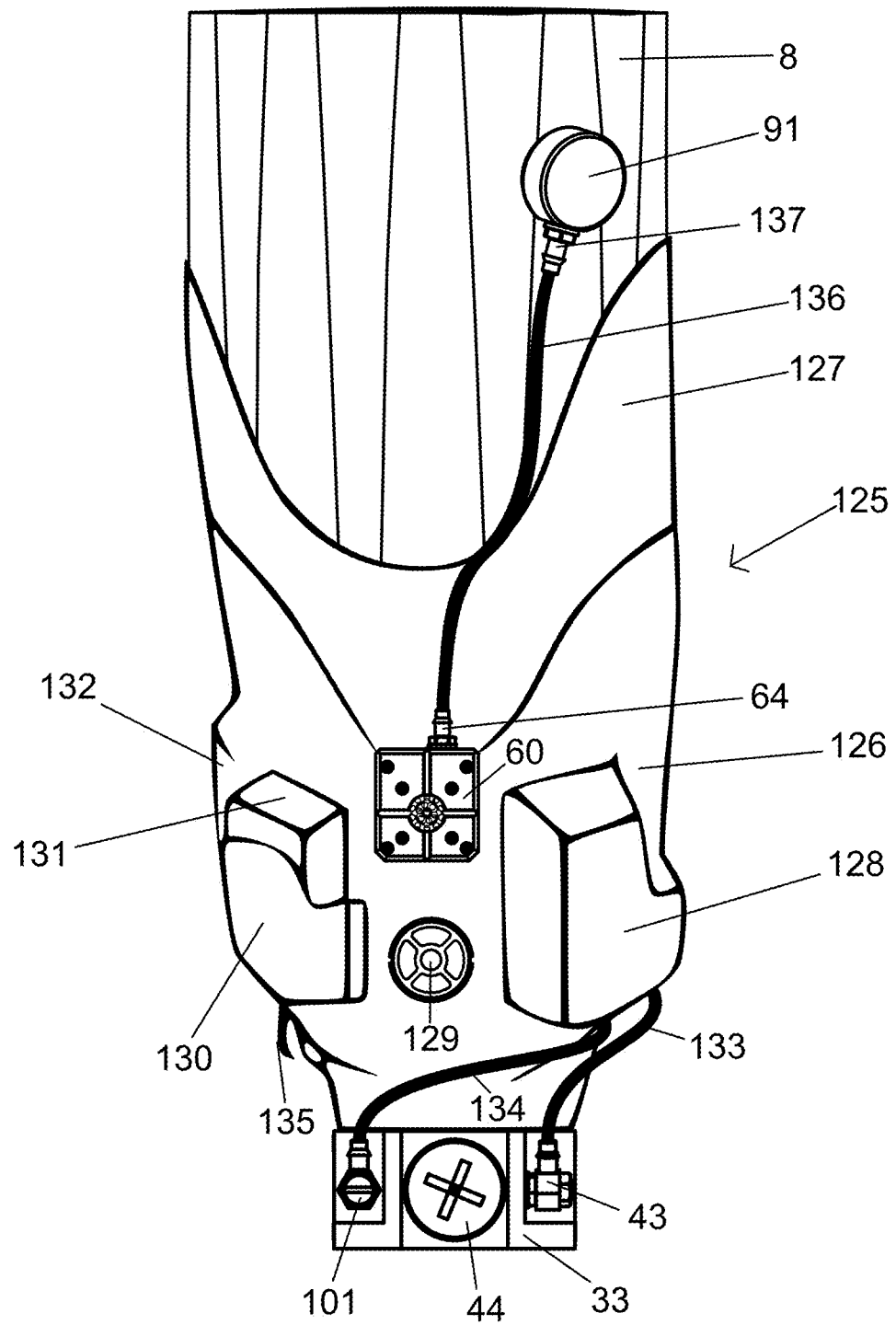
FIG. 16 is an anterior view of the over-molded enclosure for dynamic convection system components to be to be attached to a residual limb in accordance with the present invention.

Referring to FIG. 16, depicted is an assembled potential embodiment of the dynamic convection system for artificial limb. An over-molded socket system 125, which comprises an exterior composite or thermoplastic shell 126, which conforms and attaches to a rigid artificial limb socket 127, and provides an enclosure area 128 for the potential battery operated airflow generation device, system control buttons 129, a battery retaining housing with electrical connections 130 and battery 131, an area for mounting the electromechanical rising edge negative gauge binary airflow proportioning device, whose cover 60, is mounted on top of the composite or thermoplastic shell 126 and a place to retain the system circuit boards 132. For visual reference, a lock release plunger 135 is also depicted. Air into the sealed regulated environment between the residuum and the inner liner, as configured in this depiction, passes through the cove 60 and filter of the opened electromechanical binary airflow proportioning device, through one of the potential multiple electromechanical binary airflow proportioning O-ring boss straight barb fittings for tubing 64 attached to inlet air channel tubing 136, connected by the channel cap O-ring boss straight barb fittings for tubing 137 allowing fluid communication with inlet air channel cap 91 that is interfaced with the proximal air channel inflow port with occlusion preventing flange attached to the convection liner 8. The inflow air tubing 133 of the battery operated continuous airflow generating device is in fluid communication with the convection manifold housing 33 via the convection manifold O-ring boss rotating barb elbow fitting for flexible tubing 43. The convection manifold housing 33 can be universally configured in anterior and posterior placement of ports, plugs and fittings on an artificial limb. In this depiction the filter housing and spring and poppet leak prevention device threaded plug retainer 44 is assembled in an anterior placement. The battery operated continuous airflow generation device exhaust is connected via exhaust tubing 134 to an anteriorly placed industry standard face sealing elbow barb 101, which directs the exhaust flow to a series of baffles on either side of the convection manifold to minimize operational noise. The main advantage of an over-molded socket system is the advantageous weight distribution of the dynamic air exchange system. Weight placed closer to the axis of rotation has less of a pendulum effect and is better tolerated by the system user. When compared to other enclosure approaches, for example a box mounted on a pylon of the artificial limb, balance and proprioception are least disrupted by having the system component weight carried in the over-molded artificial limb socket system.

Figure 17:
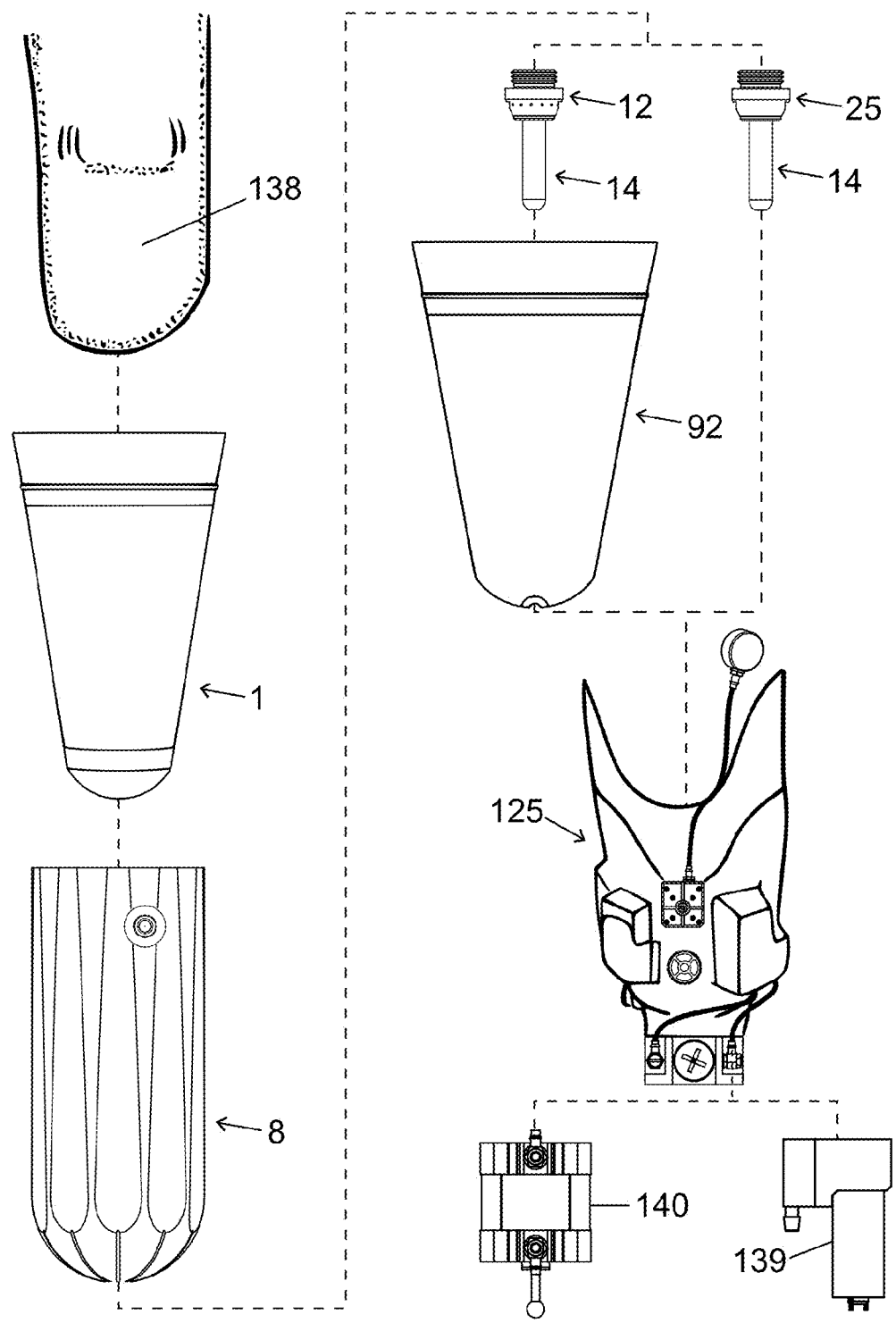
FIG. 17 is an exploded assembly sequence view of the dynamic convection system of a residual limb donning the various components and optional configurations of the system limb in accordance with the present invention.

Referring to FIG. 17, the dynamic convection system includes several unique device designs that may be appreciated alone or in system combination. Specifically depicted, an amputee's residual limb 138 will have a multi-ply textile layer with airflow seal 1, donned on it, upon which a limb conformable convection liner 8 with longitudinally scalloped convection grooves and at least one inflow and outflow air channel is further donned over the residuum 138 and multi-ply textile layer with airflow seal 1 to define an interior regulated convection environment. Optional system configurations are available to the user via different convection pin threaded adapters 12 and 25 interfacing with the convection liner and a hollow convection pin 14. A potential exterior liner textile layer with airflow seal 92, which defines a regulated negative gauge pressure environment between the outside of the convection liner 8 and the rigid socket with an over-molded socket system 125 may also be provided. The over-molded socket system houses system components, including circuit boards, battery, electromechanical airflow proportioning device in fluid communication with the at least one air inflow channel of the convection liner 8. The system user can employ a dynamic convection system configuration that uses a battery powered continuously operating airflow generation device 139 or a body powered continuously operating airflow generation device 140 or a combination of both. The body powered continuously operating airflow generation device 140 is an air cylinder configured to generate differential pressure airflow with each step of an artificial limb. It is intended to represent industry available continuously operating, while ambulating, body powered negative gauge pressure airflow generating devices.

The details and specifications of the multi-ply textile layer 1 can be found in the description of FIG. 1. The details and configuration of the convection liner 8 can be found in the description of FIG. 2A-2B, and FIG. 4A-4B. The system options offered by the convection pin threaded adapter 12 can be found in the description of FIG. 3A-3B. Likewise, the system options for the convection pin threaded adapter 25 can be found in the description of FIG. 13A-B. The details and configuration of the exterior textile layer with airflow seal 92 can be found in the description of FIG. 10. The control circuit of the electromechanical airflow proportioning device located in the over-molded socket system 125 is discussed in detail in the description of FIG. 8 and FIG. 12. Fluid connections from the electromechanical airflow proportioning device are made by convection O-ring boss straight barb fitting for tubing as depicted in FIG. 14A and FIG. 14B. An optional mechanical airflow proportioning device, which would be attached to either the convection liner 8, or the rigid socket, to which the over-molded system 125 attaches is discussed in the description of FIG. 9. The four bolt connection plate of the rigid socket, which the over-molded socket system is attached, is presented in the discussion of FIG. 5A-5B. The convection manifold's attachment and fluid communication with the four bolt connector plate is covered in the description of FIG. 6A-6B. The convection manifold, which is also in fluid communication with the circuit board and the potentially configured battery powered continuously operating airflow generation device with both its continuous inflow airflow and exhaust outflow, housed in the over-molded socket system is explored in FIG. 7A-C, and FIG. 11A-B. Fluid connections to the manifold are made by convection O-ring boss rotating barb elbow for tubing as depicted in FIG. 15A and FIG. 15B. The over-molded socket system is depicted in FIG. 16 of this specification.

This artificial limb design can be configured to be used on above knee, below knee and upper extremity amputees, as would be appreciated by those skilled in the art. Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. A forced convection system configured to be attached to a residual limb of an amputee, the system comprising:
   a conformable convection liner configured to be donned over the residual limb and define an inner regulated environment between the liner and the residual limb, the liner including a plurality of airflow convection guides on an exterior surface thereof, the plurality of airflow convection guides comprising longitudinal scalloped channels in fluid communication with respective distal airflow channels and configured to provide positive volumetric distortion within the socket during a stance phase of the amputee;
   a limb socket configured to receive the residual limb and donned liner, and together with the airflow convection guides on the exterior surface of the liner define an outer regulated environment between the socket and the liner;
   an airflow generation device coupled to the inner regulated environment and the outer regulated environment and configured to generate airflow within the inner regulated environment and the outer regulated environment; and
   a convection control system associated with the airflow generation device and configured to dynamically control airflow within the inner regulated environment and the outer regulated environment to maintain negative gauge pressure therein and transfer thermal energy therein to an external atmosphere.

2. A forced convection system configured to be attached to a residual limb of an amputee, the system comprising:
   a conformable convection liner configured to be donned over the residual limb and define an inner regulated environment between the liner and the residual limb, the liner including a plurality of airflow convection guides on an exterior surface thereof, the plurality of airflow convection guides comprising longitudinal scalloped channels in fluid communication with respective distal airflow channels and configured to provide positive volumetric distortion within the socket during a stance phase of the amputee;

a limb socket configured to receive the residual limb and donned liner, and together with the airflow convection guides on the exterior surface of the liner define an outer regulated environment between the socket and the liner;

a continuously operating airflow generation device coupled to the inner regulated environment and the outer regulated environment and configured to generate airflow within the inner regulated environment and the outer regulated environment;

a convection control system associated with the airflow generation device and configured to dynamically control airflow within the inner regulated environment and the outer regulated environment to maintain negative gauge pressure therein and transfer thermal energy therein to an external atmosphere; and a first airflow proportioning device coupled to the inner regulated environment, and a second airflow proportioning device coupled to the outer regulated environment;

wherein the convection control system includes a pressure regulation device configured to control the first and second airflow proportioning devices to open respective airflow paths to the inner and outer regulated environments; and wherein the convection control system is configured to provide regulated constant differential pressure airflow convection to the inner and outer regulated environments with the pressure regulation device, the first and second airflow proportioning devices, and the continuously operating airflow generation device.

3. The forced convection system according to claim 2, wherein the liner includes inflow air channels and at least one outflow air channel in fluid communication with the inner regulated environment; and wherein the continuously operating airflow generation device is coupled to the inner regulated environment via the inflow air channels and/or the outflow air channel.

4. The forced convection system according to claim 2, wherein the continuously operating airflow generation device comprises a battery operated continuously operating airflow generation device or a body powered continuously operating airflow generation device.

5. The forced convection system according to claim 2, further comprising a textile layer, including a proximal seal, configured to surround at least a portion of the residual limb and, with the liner, define the inner regulated environment between the liner and the residual limb.

6. The forced convection system according to claim 5, wherein the textile layer has a thickness that tapers from a distal end to a proximal end thereof.

7. The forced convection system according to claim 2, wherein the plurality of airflow convection guides on the exterior surface of the liner comprise longitudinal scalloped channels in fluid communication with respective distal airflow channels.

8. The forced convection system according to claim 7, wherein the longitudinal scalloped channels are configured to provide positive volumetric distortion within the socket during a stance phase of the amputee.

9. The forced convection system according to claim 2, wherein the liner further includes a convection pin adapter at a distal end thereof and including a central convection channel configured to provide fluid communication between the inner regulated environment and the continuously operating airflow generation device, and a plurality of adapter convection holes configured to provide fluid communication between the outer regulated environment and the central convection channel.

10. The forced convection system according to claim 9, wherein the liner further includes internal airflow convection guides on an interior surface thereof and in fluid communication with the central convection channel of the convection pin adapter at the distal end of the liner.

11. The forced convection system according to claim 9, further comprising a hollow convection pin interfaced with the convection pin adapter and including a distal outlet port in fluid communication with the central convection channel of the adapter.

12. The forced convection system according to claim 11, further comprising a convection manifold configured to interface with the hollow convection pin and including a removable absorber configured to extract moisture from airflow in an airflow path to the continuously operating airflow generation device.

13. The forced convection system according to claim 11, wherein the convection manifold includes a muffler configured to reduce noise in the airflow path.

14. The forced convection system according to claim 2, wherein each of the first and second airflow proportioning devices comprises an electromechanical binary airflow proportioning device.

15. The forced convection system according to claim 2, Wherein each of the first and second airflow proportioning devices comprises a mechanical binary airflow proportioning device.

16. The forced convection system according to claim 2, wherein the pressure regulation device comprises a rising edge triggered negative gauge pressure regulation device.

17. A method of forced convection to a residual limb of an amputee with an attached artificial limb, the method comprising:

providing a conformable convection liner to be donned over the residual limb and defining an inner regulated environment between the liner and the residual limb, the liner including a plurality of airflow convection guides on an exterior surface thereof, the plurality of airflow convection guides comprising longitudinal scalloped channels in fluid communication with respective distal airflow channels and configured to provide positive volumetric distortion within the socket during a stance phase of the amputee;

receiving the residual limb and donned liner in a limb socket, and together with the airflow convection guides on the exterior surface of the liner, defining an outer regulated environment between the socket and the liner;

coupling continuously operating airflow generation device to the inner regulated environment and the outer regulated environment and configured to generate airflow within the inner regulated environment and the outer regulated environment; and providing a convection control system with the airflow generation device to dynamically control airflow within the inner regulated environment and the outer regulated environment to maintain negative gauge pressure therein and transfer thermal energy therein to an external atmosphere; and coupling a first airflow proportioning device to the inner regulated environment, and a second airflow proportioning device to the outer regulated environment;

wherein the convection control system includes a pressure regulation device configured to control the first and second airflow proportioning devices to open respective airflow paths to the inner and outer regulated environments;

wherein the convection control system is configured to provide regulated constant differential pressure airflow convection to the inner and outer regulated environments with the pressure regulation device, the first and second airflow proportioning devices, and the continuously operating airflow generation device.

18. The method according to claim 17, wherein the liner includes inflow air channels and at least one outflow air channel in fluid communication with the inner regulated environment; and wherein the continuously operating airflow generation device is coupled to the inner regulated environment via the inflow air channels and/or the outflow air channel.

19. The method according to claim 17, wherein the continuously operating airflow generation device comprises a battery operated continuously operating airflow generation device or a body powered continuously operating airflow generation device.

20. The method according to claim 17, further comprising installing a textile layer, including a proximal seal, to surround at least a portion of the residual limb and, with the liner, define the inner regulated environment between the liner and the residual limb.

21. The method according to claim 20, wherein the textile layer has a thickness that tapers from a distal end to a proximal end thereof.

22. The method according to claim 17, wherein the plurality of airflow convection guides on the exterior surface of the liner comprise longitudinal scalloped channels in fluid communication with respective distal airflow channels.

23. The method according to claim 22, wherein the longitudinal scalloped channels are configured to provide positive volumetric distortion within the socket during a stance phase of the amputee.

24. The method according to claim 17, wherein the liner further includes a convection pin adapter at a distal end thereof and including a central convection channel configured to provide fluid communication between the inner regulated environment and the continuously operating airflow generation device, and a plurality of adapter convection holes configured to provide fluid communication between the outer regulated environment and the central convection channel.

25. The method according to claim 24, wherein the liner further includes internal convection guides on an interior surface thereof and in fluid communication with the central convection channel of the convection pin adapter at the distal end of the liner.

26. The method according to claim 24, further comprising interfacing a hollow convection pin with the convection pin adapter and including a distal outlet port in fluid communication with the central convection channel of the adapter.

27. The method according to claim 26, further comprising a convection manifold configured to interface with the hollow convection pin and including a removable absorber configured to extract moisture from airflow in an airflow path to the continuously operating airflow generation device.

28. The method according to claim 27, wherein the convection manifold includes a muffler configured to reduce noise in the airflow path.

29. The method according to claim 17, wherein each of the first and second airflow proportioning devices comprises an electromechanical binary airflow proportioning device.

30. The method according to claim 17, wherein each of the first and second airflow proportioning devices comprises a mechanical binary airflow proportioning device.

31. The method according to claim 17, wherein the pressure regulation device comprises a rising edge triggered negative gauge pressure regulation device.

* * * * *